(12) United States Patent
Sandford et al.

(10) Patent No.: US 10,995,075 B2
(45) Date of Patent: May 4, 2021

(54) PROCESS FOR PRODUCING FLUOROCYTOSINE AND FLUOROCYTOSINE DERIVATIVES

(71) Applicant: UNIVERSITY OF DURHAM, Durham (GB)

(72) Inventors: Graham Sandford, Durham (GB); Antal Harsanyi, Durham (GB)

(73) Assignee: University of Durham

( * ) Notice: Subject to any disclaimer, the term of this patent is extended or adjusted under 35 U.S.C. 154(b) by 0 days.

(21) Appl. No.: 16/544,067

(22) Filed: Aug. 19, 2019

(65) Prior Publication Data
US 2020/0095207 A1 Mar. 26, 2020

Related U.S. Application Data

(63) Continuation of application No. 15/507,342, filed as application No. PCT/GB2015/052342 on Aug. 13, 2015, now abandoned.

(30) Foreign Application Priority Data

Aug. 29, 2014 (GB) .................................. 1415317

(51) Int. Cl.
C07D 239/47 (2006.01)

(52) U.S. Cl.
CPC .................................. *C07D 239/47* (2013.01)

(58) Field of Classification Search
CPC .................................................. C07D 239/47
See application file for complete search history.

(56) References Cited

U.S. PATENT DOCUMENTS

| | | | |
|---|---|---|---|
| 2,945,038 | A | 7/1960 | Hoffman La Roche |
| 4,029,661 | A | 6/1977 | Schuman et al. |
| 4,473,691 | A | 9/1984 | Takahara |
| 5,789,580 | A | 8/1998 | Chambers |
| 5,859,255 | A | 1/1999 | Chambers |
| 2005/0214184 | A1 | 9/2005 | Chambers |

FOREIGN PATENT DOCUMENTS

| | | |
|---|---|---|
| EP | 0181589 | 5/1986 |
| JP | 56095173 | 8/1981 |
| JP | 57154171 | 9/1982 |

OTHER PUBLICATIONS

Cecilia C.P. Da Silva et al. "The continuum in 5-Fluorocytosine. Toward Salt Formation" Crystal Growth and Design, vol. 13, No. 10, Oct. 2, 2013 pp. 4315-4322, XP055216270.

Marcus Baumann et al. "Development of fluorination methods using continuous-flow microreactors" Tetrahedron, Elsevier Science Publishers. Amsterdam NL vol. 65, No. 33, Aug. 15, 2009, pp. 6611-6625. XP025321065.
Vermes et al. 46 Journal of Antimicrobial Chemotherapy, 171-179 (2000).
R. D. Chambers et al. "Elemental fluorine part 13. Gas-liquid thin film microreactors for selective direct fluorination", Lab on a Chip, 1, 132-137 (2001).
C.B. Mcpake et al. 16 Organic Process Research & Development, 844-851 (2012).
R. D. Chambers et al. Journal of the Chemical Society, Perkin Transactions 1: Organic and Bio-Organic Chemistry, 605-609 (1996).
G. Visser et al. Journal of the Chemical Society, Perkin Transactions 1: Organic and Bio-Organic Chemistry, 1203-1207 (1988).
N. G. Anderson. Practical Process & Research Development 269-289 (2000).
R. L. Hartman et al. 50 Angewandte Chemie International Edition, 7502-7519 (2011).
C. Wiles et al. European Journal of Organic Chemistry, 1655-1671 (2008).
L. Malet-Sanz et al. 55 Journal of Medicinal Chemistry 4062-4098 (2012).
G. F. Klein. Pharmaceutical Technology Today (1999).
N . De. Mas et al. 48 Industrial Engineering and Chemical Research, 1428-1434 (2009).
G. Visser et al. 51 Journal of Organic Chemistry, 1466-1471 (1986).
R. D. Chambers et al. "Direct fluorination of 1,3-dicarbonyl compounds" Tetrahedron 52, 1-8 (1996).
C. B. Mcpake et al. "Continuous Flow Synthesis of Difluoroamine Systems by Direct Fluorination" Aust. J. Chem. 2013, 66, 145-150.
C. B. Mcpake et al. "Sequential Continuous Flow Processes for the Oxidation of Amines and Azides by using HOF.MeCN" Chem.Sus.Chem., 2012, 5, 312-319.

*Primary Examiner* — Paul V Ward
(74) *Attorney, Agent, or Firm* — King & Spalding

(57) ABSTRACT

The present invention relates to a method of manufacturing a fluorocytosine-based compound of Formula I.

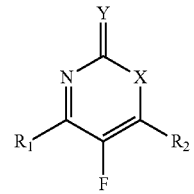

(Formula I)

The invention also relates to a compound obtained by such a method, a pharmaceutical drug substance and a method for its manufacture, a pharmaceutical composition, and also various uses in therapy of the compounds, pharmaceutical drug substances, and pharmaceutical compositions of the invention.

20 Claims, 7 Drawing Sheets

19130832.12.fid
GS:TH:B116-2 PURIFIED
$^{13}$CNMR (101 MHz, Deuterium Oxide) δ 153.65 (d,J=23.4 Hz), 147.88 (d,J=232.3 Hz,), 130.66(d,J=29.8 Hz)

PROCESS FOR PRODUCING FLUOROCYTOSINE AND FLUOROCYTOSINE DERIVATIVES

INTRODUCTION

The present invention relates to a method of manufacturing a compound, especially a fluorocytosine-based compound. The invention also relates to a compound obtained by such a method, a pharmaceutical drug substance and a method for its manufacture, a pharmaceutical composition, and also various uses in therapy of the compounds, pharmaceutical drug substances, and pharmaceutical compositions of the invention.

BACKGROUND

Flucytosine was approved by the FDA in 1971 (Ancoban®, Valeant) for the treatment of fungal infections. 5-Fluorocytosine (Flucytosine) is an important antimycotic drug in its own right but is also an intermediate in the synthesis of Capecitabine (anti-cancer) and Emtricitabine (anti-HIV).

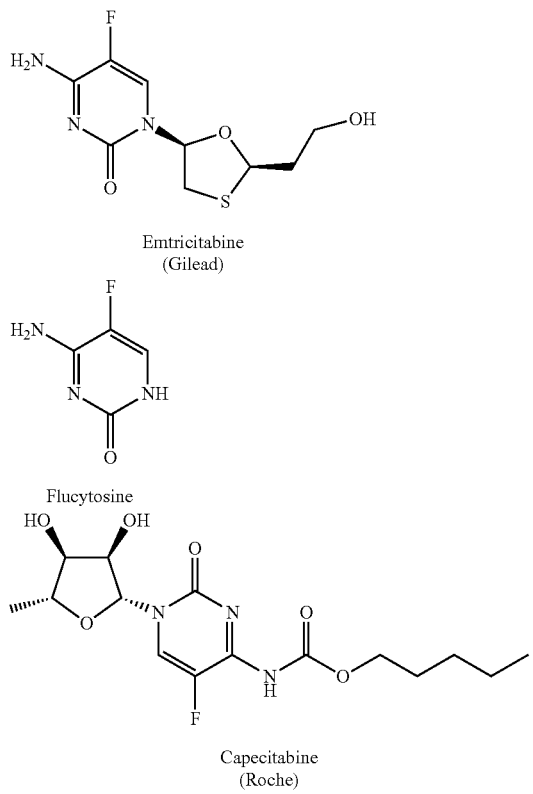

Emtricitabine
(Gilead)

Flucytosine

Capecitabine
(Roche)

Of the few reported flucytosine syntheses, only routes utilising 5-fluorouracil (5-FU) as starting material appear to have been used in manufacturing. This process relies on the availability of 5-FU, which is prepared on the manufacturing scale via direct fluorination of uracil. There are numerous syntheses of uracil in the literature, but only one of these has the potential for scale-up and involves reaction of malic acid and urea in fuming sulfuric acid.

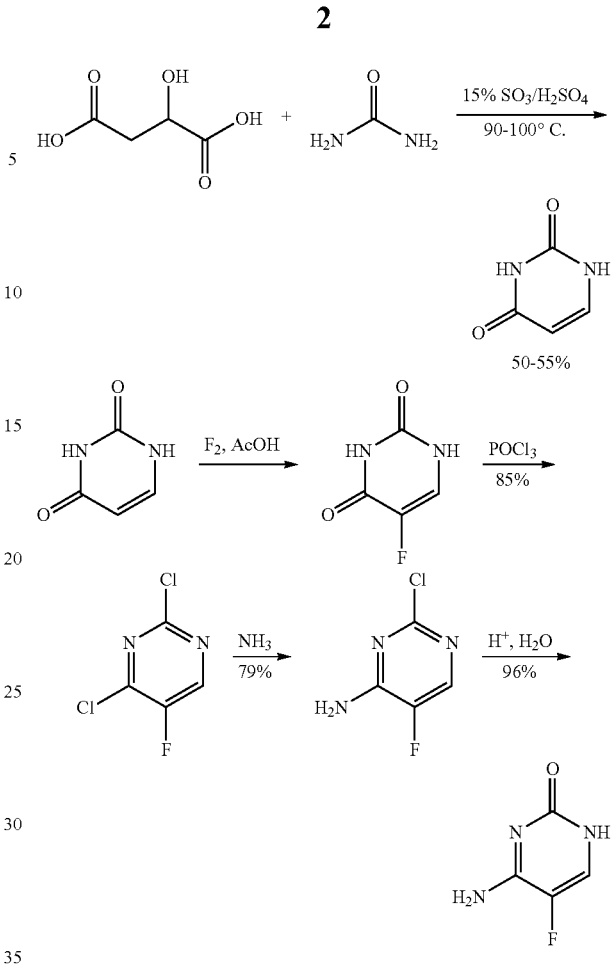

A Hoffmann-la-Roche patent (U.S. Pat. No. 2,945,038) describes synthetic processes involving 5-FU being treated with $POCl_3$ and dimethylaniline to yield 2,4-dichloro-5-fluoropyrimidine in good yield after distillation. This intermediate is reacted with aqueous ammonia solution and hydrolysed in concentrated hydrochloric acid, to yield 5-fluorocytosine from 5-fluorouracil in an overall 64% yield (3 steps from 5-FU) (see reaction scheme above).

Overall, this scheme represents a 5 step process to Flucytosine.

Based on data from the Roche patent (U.S. Pat. No. 2,945,038) the PMI metrics of the industrial method can be assessed for the 3 steps from 5-FU. Our analysis shows that the process is relatively good in terms of solvent use, but the amount of reagents used is very high. The overall PMI from 5-fluorouracil to 5-fluorocytosine is 87, (i.e. 1 kg of product uses 87 kg of material and also uses a significant amount of energy).

In another procedure from Bayer (EP0181589), 2,5-difluoro-4,6-dichloropyrimidine is used in a similar multistep process (dechlorination-amination-hydrolysis) to afford the desired product[i] although the synthesis of 2,5-difluoro-4,6-dichloropyrimidine is a complex, multistep process and so we need not consider this route further.

To address the problems inherent with the prior art, the inventors investigated producing flucytosine via direct fluorination of cytosine. However, the inventors noted that they were always faced with a dilemma between achieving high yields (but low purity) or low yields (but high purity).

Cytosine reacts with fluorine gas to produce flucytosine and a difluoro impurity. The inventors generally found that the difluoro impurity could be removed by recrystalisation. However, if cytosine starting material remained in the crude reaction mixture, this was always extremely difficult to remove. Therefore, it is desirable to ensure that the reaction proceeds to 100% completion, for instance by using excess fluorine. However, in driving the reaction to completion, increased quantities of the difluoro impurity were formed, which in turn compromises the yield of fluocytosine. Without wishing to be bound by theory, it is thought that compounds comprising a cytosine-like core will suffer from the same shortcomings.

It is therefore an object of the invention to provide an improved fluorination process in respect of cytosine or cytosine-based compounds, especially with respect to overall yields and purities. However, it is also suitably an object of the invention to provide a more environmentally friendly process. Moreover, it is also suitably an object of the invention to provide a process with one or more improvements selected from: improved overall PMI, reduced costs, reduced labour, reduced waste.

SUMMARY OF THE INVENTION

According to a first aspect of the present invention there is provided a method of manufacturing a compound of Formula I (or a salt, solvate, or synthetic equivalent thereof):

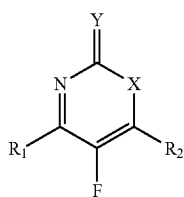

(Formula I)

the method comprising reacting a compound of Formula II (or a salt, solvate, or synthetic equivalent thereof):

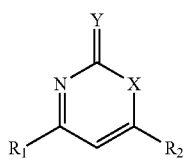

(Formula II)

with an electrophilic fluorinating agent;
wherein:

X is $NR_x$, O, or S; wherein $R_x$ is hydrogen or is independently selected from any $R_N$ group;

Y is O, S, or $NR_y$; wherein $R_y$ is hydrogen or is independently selected from any $R_N$ group;

$R_1$ is hydrogen or is independently selected from any $R_s$ group, though most suitably $R_1$ is an electron donating group (EDG), most suitably an EDG selected from $NR_{1a}R_{1b}$ or $OR_{1a}$, wherein $R_{1a}$ and $R_{1b}$ are each independently selected from hydrogen or any $R_N$ group;

$R_2$ hydrogen or is independently selected from any $R_s$ group;

each $R_N$ group is independently selected from (1-8C) alkyl, (2-8C)alkenyl, (2-8C)alkynyl, aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, formyl, carboxy, (2-6C)alkanoyl, (1-6C) alkoxycarbonyl, carbamoyl, N-(1-6C)alkylcarbamoyl, N,N-di-[(1-6C)alkyl]carbamoyl, (1-6C)alkylsulphinyl, (1-6C) alkylsulphonyl, N-(1-6C)alkylsulphamoyl, N,N-di-[(1-6C) alkyl]sulphamoyl; wherein each $R_N$ group is optionally independently substituted with one or more $R_s$ groups;

each $R_s$ group is independently selected from halogeno, trifluoromethyl, cyano, isocyano, nitro, hydroxy, mercapto, amino, formyl, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (1-6C) alkoxycarbonyloxy, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, (1-6C)alkoxycarbonylamino, N-(1-6C)alkyl-(1-6C) alkoxycarbonylamino, N'-(1-6C)alkylureido, N',N'-di-[(1-6C)alkyl]ureido, N-(1-6C)alkylureido, N,N'-di-[(1-6C) alkyl]ureido, N,N',N'-tri-[(1-6C)alkyl]ureido, N-(1-6C) alkylsulphamoyl, N,N-di-[(1-6C)alkyl]sulphamoyl, (1-6C) alkanesulphonylamino and N-(1-6C)alkyl-(1-6C) alkanesulphonylamino, or from a group of the formula:

$$L_1-Q_1$$

wherein $L_1$ is a direct bond or is selected from $(CR_{L1}R_{L2})_n$, O, S, SO, $SO_2$, $N(R_{L1})$, CO, $CR_{L1}(O\ R_{L2})$, $CON(R_{L1})$, $N(R_{L1})CO$, $N(R_{L1})C(O)O$, $N(R_{L1})CON(R_{L2})$, $SO_2N(R_{L1})$, $N(R_{L1})SO_2$, $OC(R_{L1})_2$, $SC(R_{L1})_2$ and $N(R_{L1})C(R_{L2})_2$, wherein n is an integer between 1 and 3, and wherein $R_{L1}$ and $R_{L2}$ are each independently hydrogen or (1-8C)alkyl;

and $Q_1$ is (1-8C)alkyl, (2-8C)alkenyl, (2-8C)alkynyl, aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl;

and wherein any $R_s$ group is independently optionally further substituted by one or more $R_s$ groups (i.e. first order $R_s$ substitutent groups in relation to any given "parent" $R_s$ group), wherein any first order $R_s$ substitutent group is optionally independently further substituted by one or more $R_s$ groups (i.e. second order $R_s$ substituent groups in relation to any given "parent" $R_s$ group), though suitably optional further substituents do not extend beyond second order optional substituents (i.e. second order $R_s$ substituents are the highest order, suitably first order $R_s$ substituents are the highest order); wherein the reaction between the compound of Formula II and the electrophilic fluorinating agent is performed in a continuous flow reactor.

According to a further aspect of the present invention there is provided a compound of Formula I (or a salt, solvate, or synthetic equivalent thereof) obtainable by, obtained by, or directly obtained by the method of manufacturing a compound of Formula I as defined herein.

According to a further aspect of the present invention there is provided a compound of Formula I (or a salt, solvate, or synthetic equivalent thereof), comprising less than or equal to 1 wt % of a compound of Formula II, (or a salt, solvate, or synthetic equivalent thereof).

According to a further aspect of the present invention there is provided a composition of a compound of Formula I (or a salt, solvate, or synthetic equivalent thereof), the composition comprising a compound of Formula I (or a salt, solvate, or synthetic equivalent thereof); wherein the composition either: a) is free of a compound of Formula II (or a salt, solvate, or synthetic equivalent thereof), or b) comprises a compound of Formula II (or a salt, solvate, or synthetic equivalent thereof) in a weight ratio to the compound of Formula I of less than or equal to 1:100.

According to a further aspect of the present invention there is provided a (pharmaceutical) composition comprising a compound of Formula I (or a salt, solvate, or synthetic equivalent thereof) or a composition of a compound of Formula I (or a salt, solvate, or synthetic equivalent thereof) as defined herein (suitably additionally comprising a pharmaceutically acceptable diluent or carrier).

According to a further aspect of the present invention there is provided a continuous flow apparatus comprising a continuous flow reactor as defined herein (and optionally any other features defined herein in relation to the continuous flow reactor) configured to, adapted to, or suitable to carry out the method(s) of the invention as defined herein.

According to a further aspect of the present invention there is provided a method of manufacturing a pharmaceutical drug substance (or a pharmaceutically acceptable salt, solvate, or synthetic equivalent thereof), the method comprising: reacting a compound of Formula II (or a salt, solvate, or synthetic equivalent thereof):

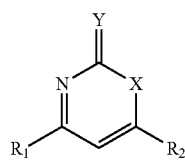

(Formula II)

with an electrophilic fluorinating agent to produce a compound of Formula I (or a pharmaceutically acceptable salt, solvate, or synthetic equivalent thereof):

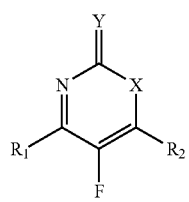

(Formula I)

and optionally thereafter performing one or more further step or steps to produce the pharmaceutical drug substance (or a pharmaceutically acceptable salt, solvate, or synthetic equivalent thereof);
wherein X, Y, $R_1$, $R_2$, and any groups associated therewith are as defined herein; wherein the reaction between the compound of Formula II and the electrophilic fluorinating agent is performed in a continuous flow reactor.

According to a further aspect of the present invention there is provided a pharmaceutical drug substance (or a pharmaceutically acceptable salt, solvate, or synthetic equivalent thereof) obtainable by, obtained by, or directly obtained by the method of manufacturing a pharmaceutical drug substance as defined herein.

According to a further aspect of the present invention there is provided a pharmaceutical drug substance (or a pharmaceutically acceptable salt, solvate, or synthetic equivalent thereof), comprising less than or equal to 1 wt % of a non-fluorinated analog (or impurity) of the pharmaceutical drug substance (or a pharmaceutically acceptable salt, solvate, or synthetic equivalent thereof).

According to a further aspect of the present invention there is provided a pharmaceutical drug substance (or a pharmaceutically acceptable salt, solvate, or synthetic equivalent thereof), the composition comprising a pharmaceutical drug substance (or a pharmaceutically acceptable salt, solvate, or synthetic equivalent thereof); wherein the composition either: a) is free of a non-fluorinated analog (or impurity) of the pharmaceutical drug substance (or a pharmaceutically acceptable salt, solvate, or synthetic equivalent thereof), or b) comprises a non-fluorinated analog (or impurity) of the pharmaceutical drug substance (or a pharmaceutically acceptable salt, solvate, or synthetic equivalent thereof) in a weight ratio to the compound of Formula I of less than or equal to 1:100.

According to a further aspect of the present invention there is provided a (pharmaceutical) composition comprising a pharmaceutical drug substance (or a pharmaceutically acceptable salt, solvate, or synthetic equivalent thereof) or a composition a pharmaceutical drug substance (or a pharmaceutically acceptable salt, solvate, or synthetic equivalent thereof) as defined herein (suitably additionally comprising a pharmaceutically acceptable diluent or carrier).

According to a further aspect of the present invention, there is provided a compound of Formula I (or a pharmaceutically acceptable salt, solvate, or synthetic equivalent thereof), or a composition thereof, as defined herein for use in therapy.

According to a further aspect of the present invention, there is provided a method of treating a medical condition or medical disorder in a patient in need of such treatment, said method comprising administering to said patient a therapeutically effective amount of a compound of Formula I (or a pharmaceutically acceptable salt, solvate, or synthetic equivalent thereof), or a composition thereof, as defined herein.

According to a further aspect of the present invention, there is provided a use of a compound of Formula I (or a pharmaceutically acceptable salt, solvate, or synthetic equivalent thereof), or a composition thereof, as defined herein in the manufacture of a medicament.

According to a further aspect of the present invention, there is provided a compound of Formula I (or a pharmaceutically acceptable salt, solvate, or synthetic equivalent thereof), or a composition thereof, as defined herein for use in the treatment of an infection (especially a fungal infection), for example, infections caused by susceptible strains of *Candida* or *Cryptococcus neoformans*, chromomycosis, and cystitis; or for use in the treatment of a proliferative disorder (e.g. cancer), for example, colorectal cancer, breast cancer, gastric cancer, oesophageal cancer; or for use in the treatment of human immunodeficiency virus (HIV) infection, acquired immunodeficiency syndrome (AIDS), and/or hepatitis B virus (HBV) infection.

According to a further aspect of the present invention, there is provided a method of treating an infection (especially a fungal infection), for example, infections caused by susceptible strains of *Candida* or *Cryptococcus neoformans*, chromomycosis, and cystitis; or a method of treating a proliferative disorder (e.g. cancer), for example, colorectal cancer, breast cancer, gastric cancer, oesophageal cancer; or a method of treating human immunodeficiency virus (HIV) infection, acquired immunodeficiency syndrome (AIDS), and/or hepatitis B virus (HBV) infection; in a patient in need of such treatment, said method comprising administering to said patient a therapeutically effective amount of a compound of Formula I (or a pharmaceutically acceptable salt, solvate, or synthetic equivalent thereof), or a composition thereof, as defined herein.

According to a further aspect of the present invention, there is provided a use of a compound of Formula I (or a pharmaceutically acceptable salt, solvate, or synthetic equivalent thereof), or a composition thereof, as defined herein in the manufacture of a medicament for the treatment of an infection (especially a fungal infection), for example, infections caused by susceptible strains of *Candida* or *Cryptococcus neoformans*, chromomycosis, and cystitis; or for the treatment of a proliferative disorder (e.g. cancer), for example, colorectal cancer, breast cancer, gastric cancer, oesophageal cancer; or for the treatment of human immunodeficiency virus (HIV) infection, acquired immunodeficiency syndrome (AIDS), and/or hepatitis B virus (HBV) infection.

According to a further aspect of the present invention, there is provided a pharmaceutical drug substance (or a pharmaceutically acceptable salt, solvate, or synthetic equivalent thereof), or a composition thereof, as defined herein for use in therapy.

According to a further aspect of the present invention, there is provided a method of treating a medical condition or medical disorder in a patient in need of such treatment, said method comprising administering to said patient a therapeutically effective amount of a pharmaceutical drug substance (or a pharmaceutically acceptable salt, solvate, or synthetic equivalent thereof), or a composition thereof, as defined herein.

According to a further aspect of the present invention, there is provided a use of a pharmaceutical drug substance (or a pharmaceutically acceptable salt, solvate, or synthetic equivalent thereof), or a composition thereof, as defined herein in the manufacture of a medicament.

According to a further aspect of the present invention, there is provided a pharmaceutical drug substance (or a pharmaceutically acceptable salt, solvate, or synthetic equivalent thereof), or a composition thereof, as defined herein for use in the treatment of an infection (especially a fungal infection), for example, infections caused by susceptible strains of *Candida* or *Cryptococcus neoformans*, chromomycosis, and cystitis; or for use in the treatment of a proliferative disorder (e.g. cancer), for example, colorectal cancer, breast cancer, gastric cancer, oesophageal cancer; or for use in the treatment of human immunodeficiency virus (HIV) infection, acquired immunodeficiency syndrome (AIDS), and/or hepatitis B virus (HBV) infection.

According to a further aspect of the present invention, there is provided a method of treating an infection (especially a fungal infection), for example, infections caused by susceptible strains of *Candida* or *Cryptococcus neoformans*, chromomycosis, and cystitis; or a method of treating a proliferative disorder (e.g. cancer), for example, colorectal cancer, breast cancer, gastric cancer, oesophageal cancer; or a method of treating human immunodeficiency virus (HIV) infection, acquired immunodeficiency syndrome (AIDS), and/or hepatitis B virus (HBV) infection; in a patient in need of such treatment, said method comprising administering to said patient a therapeutically effective amount of a pharmaceutical drug substance (or a pharmaceutically acceptable salt, solvate, or synthetic equivalent thereof), or a composition thereof, as defined herein.

According to a further aspect of the present invention, there is provided a use of a pharmaceutical drug substance (or a pharmaceutically acceptable salt, solvate, or synthetic equivalent thereof), or a composition thereof, as defined herein in the manufacture of a medicament for the treatment of an infection (especially a fungal infection), for example, infections caused by susceptible strains of *Candida* or *Cryptococcus neoformans*, chromomycosis, and cystitisor; for the treatment of a proliferative disorder (e.g. cancer), for example, colorectal cancer, breast cancer, gastric cancer, oesophageal cancer; or for the treatment of human immunodeficiency virus (HIV) infection, acquired immunodeficiency syndrome (AIDS), and/or hepatitis B virus (HBV) infection.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

DETAILED DESCRIPTION OF THE INVENTION

Definitions

Figure 1:
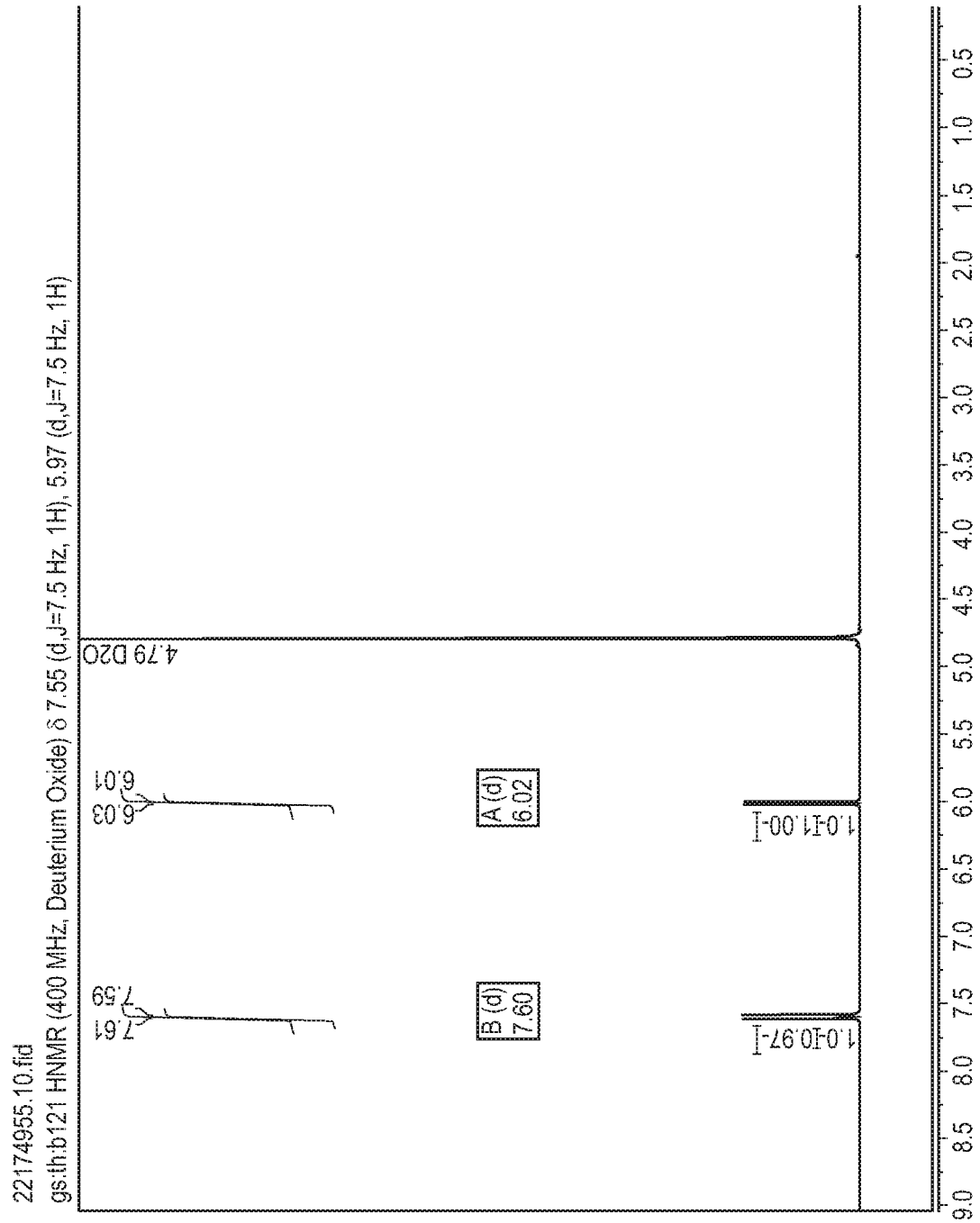
FIG. 1 shows a $^1$H NMR of crude non-recrystallised cytosine.

Unless otherwise stated, the following terms used in the specification and claims have the following meanings set out below.

Herein, the term "compound of Formula [X]", where [X] is a number, typically a roman numeral optionally followed by an alphanumeric character, may be abbreviated to "compound [X]". A reference to either a "compound of Formula [X]" or "compound [X]" suitably includes a salt (e.g. pharmaceutically acceptable salt) or solvate (e.g. hydrate) thereof, and suitably also includes a synthetic equivalent thereof.

Herein, unless stated otherwise, all chemical nomenclature may be defined in accordance with IUPAC definitions.

Herein, the term "hydrocarbon" is well understood in the art, and refers to compounds containing carbon and hydrogen only. The term "hydrocarbyl" general refers any aliphatic, acyclic, or cyclic (including aryl) hydrocarbon group, suitably with no heteroatoms. Such compounds include, inter alia, alkanes, alkenes, alkynes, arenes, and cyclic versions thereof. The term "hydrocarbon" anthracene, naphthalene, benzene, and/or derivatives thereof (e.g. toluene).

Herein, the term "carbocyclyl", "carbocycle" or "carbocyclic" refers to a radical of a non-aromatic cyclic hydrocarbon group, generally having from 3 to 10 ring carbon atoms (i.e. (3-10C)carbocyclyl) and zero heteroatoms in the non-aromatic ring system. Suitably, carbocyclyl groups include (3-nC)cycloalkyl and (3-nC)cycloalkenyl. Exemplary embodiments include: cyclobutyl, cyclobutenyl, cyclopentyl, cyclopentenyl, cyclohexyl, cyclohexenyl, cyclohexadienyl, cycloheptyl, cycloheptenyl, cycloheptadienyl, cycloheptatrienyl, cyclooctyl, cyclooctenyl, bicyclo[2.2.1]heptanyl, bicyclo[2.2.2]octanyl, and the like.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-5C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

Wherever groups with large carbon chains are disclosed (e.g. (1-12C)alkyl, (1-8C)alkenyl, etc.), such groups may optionally be shortened, for instance containing a between 1 and 5 carbons (e.g. (1-5C)alkyl or (1-5C)alkenyl), or contain between 1 and 3 carbons (e.g. (1-3C)alkyl or (1-3C)alkenyl instead of (1-12C)alkyl or (1-8C)alkenyl).

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess telomerase inhibitory activity.

The present invention also encompasses compounds of the invention as defined herein which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and O may be in any isotopic form, including $^{16}$O and $^{18}$O; and the like.

It is also to be understood that certain compounds of the formula I may exhibit polymorphism, and that the invention encompasses all such forms.

Compounds may exist in a number of different tautomeric forms and references to compounds include all such forms. For the avoidance of doubt, where a compound can exist in one of several tautomeric forms, and only one is specifically described or shown, all others are nevertheless embraced by the definition of the compound. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

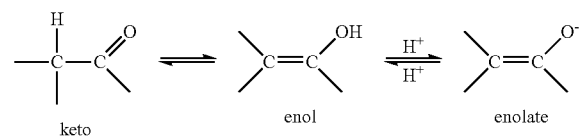

keto      enol      enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N-$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl) piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Unless stated otherwise, references herein to a "pKa" should be construed as a pKa value in water at standard ambient temperature and pressure (SATP), suitably of the conjugate acid of the relevant species.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw; parts by moles) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "substantially free", when used in relation to a given component of a composition, refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition, refers to a composition containing none of said component.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The invention concerns amongst other things general and particular medical treatments as defined herein. The term "treatment", and the therapies encompassed by this invention, include the following and combinations thereof: (1) inhibiting, e.g. delaying initiation and/or progression of, an event, state, disorder or condition, for example arresting, reducing or delaying the development of the event, state, disorder or condition, or a relapse thereof in case of maintenance treatment or secondary prophylaxis, or of at least one clinical or subclinical symptom thereof; (2) preventing or delaying the appearance of clinical symptoms of an event, state, disorder or condition developing in an animal (e.g. human) that may be afflicted with or predisposed to the state, disorder or condition but does not yet experience or display clinical or subclinical symptoms of the state, disorder or condition; and/or (3) relieving and/or curing an event, state, disorder or condition (e.g., causing regression of the event, state, disorder or condition or at least one of its clinical or subclinical symptoms, curing a patient or putting a patient into remission). The benefit to a patient to be treated may be either statistically significant or at least perceptible to the patient or to the physician. It will be understood that a medicament will not necessarily produce a clinical effect in each patient to whom it is administered; thus, in any individual patient or even in a particular patient population, a treatment may fail or be successful only in part, and the meanings of the terms "treatment", "prophylaxis" and "inhibitor" and of cognate terms are to be understood accordingly. The compositions and methods described herein are of use for therapy and/or prophylaxis of the mentioned conditions.

The term "prophylaxis" includes reference to treatment therapies for the purpose of preserving health or inhibiting or delaying the initiation and/or progression of an event, state, disorder or condition, for example for the purpose of reducing the chance of an event, state, disorder or condition occurring. The outcome of the prophylaxis may be, for example, preservation of health or delaying the initiation and/or progression of an event, state, disorder or condition. It will be recalled that, in any individual patient or even in a particular patient population, a treatment may fail, and this paragraph is to be understood accordingly.

The term "inhibit" includes reference to delaying, stopping, reducing the incidence of, reducing the risk of and/or reducing the severity of an event, state, disorder or condition. Inhibiting an event, state, disorder or condition may therefore include delaying or stopping initiation and/or progression of such, and reducing the risk of such occurring. The products of the disclosure may be used to inhibit events, disorders and/or conditions which are disclosed herein.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Routes of administration useful in the disclosed methods include but are not limited to oral and parenteral routes, such as intravenous (iv), intraperitoneal (ip), rectal, topical, ophthalmic, nasal, and transdermal.

GENERAL METHODOLOGY AND ADVANTAGES OF THE INVENTION

The inventive method of manufacturing a compound of Formula I (or a salt, solvate, or synthetic equivalent thereof) may be described by the reaction scheme of Scheme 1. In line with the invention, such a method may also be used to form a variety of pharmaceutical drug substances incorporating the relevant molecular core (i.e. defined by formula I), such as flucytosine (N-unsubstituted), emtricitabine (internal N-substituted), and capecitabine (N,N-disubstituted). G

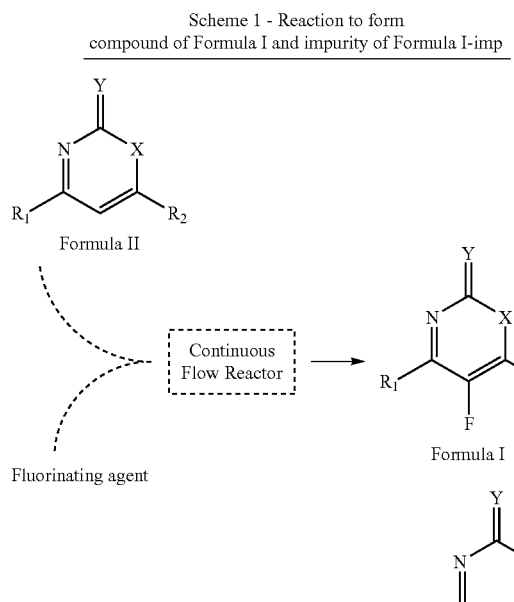

Scheme 1 - Reaction to form compound of Formula I and impurity of Formula I-imp

The method involves monofluorination of the compound II to produce the compound I. Since it is typically problematic to separate compound I (product) from compound II (starting material) (e.g. during purification and/or isolation of compound I) and thus difficult to obtain pure compound I from a mixture of compounds I and II, the fluorination reaction upon compound II is suitably driven (substantially) to completion (suitably at least 99% completion, most suitably 100% completion). This allows compound I to be isolated from a crude reaction mixture in a (substantially) pure form, with minimal contamination by compound II. However, prior to the advent of the present invention, such monofluorination (especially where compound II is substantially all consumed during the fluorination reaction) would inevitably result in the formation of substantial quantities of the compound of Formula I-imp.

Compound I-imp is a difluorinated analog (or impurity) of compound I. Without wishing to be bound by theory, it is thought that compound I-imp is formed by fluorination of compound I, a reaction which may compete with fluorination of compound II. Though compound I is generally readily separable from compound I-imp (e.g. during purification and/or isolation of compound I), the "over-fluorination" that leads to compound I-imp compromises the yield of compound I. Such fluorinations have therefore traditionally been a compromise between purity and yield, since an improvement in one of these generally compromises the other.

However, the method of the present invention, affords a surprisingly significant reduction in compound I-imp formation under conditions which allow the fluorination reaction to be drive (substantially) to completion (i.e. to consume substantially all of compound II). This allows high yields of highly pure compound I. Such a methodology also allows for the synthesis of compounds of formula I in a minimal number of steps from readily available inexpensive commodity chemicals. The combination of synthetic methodology (e.g. that the fluorination step is a downstream step, nearer to the end of the synthesis) and reaction conditions (e.g. continuous flow) also allows the amounts of electrophilic fluorinating agent to be minimised, thus reducing both hazard and toxic waste levels. Overall the reaction conditions and consequential waste streams are more environmentally benign, thus providing a significantly more commercially and environmentally viable synthesis of compounds of Formula I. Despite the long-felt need for improved syntheses of compounds of formula I (especially for the pharmaceutical industry), not least in view of the prevailing undesirable yield vs purity compromises, this combination of advantages was completely unforeseeable, especially given the complex interplay of variables. Without wishing to be bound by theory, it is now thought that the particular molecular cores which characterise compounds I and II give rise to the unique dual problem of difluorination and separation of starting material (compound II) and product (compound I), which is solved by the method of the invention.

General Points Regarding Methods of Manufacture

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be understood by the skilled person that the compounds of the invention, such as a compound of Formula I or pharmaceutical drug substance (or salt, solvate, or synthetic equivalent thereof) can be isolated and purified using techniques well known in the art. This may include an appropriate work-up procedure (optionally including quenching, pH adjustment, washes, drying, etc.). This may include concentration (e.g. in vacuo), recrystallisation, chromatography (whether standard or reverse-phase). Purity may be verified by techniques well known in the art.

In the context of the invention, a "synthetic equivalent" is well understood by those skilled in the art, especially in the art of retrosynthesis, as a reference to a compound (or compounds) corresponding with a given "synthon" (E. J. Corey, *Pure App. Chem.*, 1967, 14: 30-37). Any given synthon may have a plurality of synthetic equivalents and, as such, a given first synthetic equivalent may be considered a synthetic equivalent of a second synthetic equivalent, though each of the two synthetic equivalents naturally correspond with a common synthon. As will be appreciated by those skilled in the art, a synthon is (typically) a hypothetical structural unit, fragment, or synthetic building block relating to a potential synthetic operation (E. J. Corey, "Robert Robinson Lecture. Retrosynthetic thinking-essentials and examples", *Chem. Soc. Rev.*, 1988, 17: 111-133). In the context of the present invention, alternative synthetic equivalents of any given compound or synthon are suitably independently transformable into an identical compound, be it into the given compound itself or most suitably a derivative (or post-reacted form) thereof. However, the skilled person will readily appreciate that transforming alternative synthetic equivalents into an identical compound may require a different process, and potentially a different number of synthetic steps. In the context of the invention, both starting materials and products may be designated by reference to a corresponding synthetic equivalent thereof, since it will be understood that any two synthetically equivalent starting materials may be ultimately transformed into an identical product or into a product which may thereafter be transformed into an identical product. Synthetic equivalents may be particularly relevant in the context of protecting groups, which may be transiently incorporated into part of the molecular structure of a compound (especially a part of said molecule which may be vulnerable or sensitive during processing) in order that they can be removed once having served their protective function. As such, the method of the invention may optionally comprise any one or more of:

- transforming a synthetic equivalent of the compound of Formula II (or a salt or solvate thereof) into a compound of Formula II (or a salt or solvate thereof), suitably via one or more suitable chemical transformations (e.g. deprotections);
- transforming a synthetic equivalent of the compound of Formula II (or a salt or solvate thereof) into a compound of Formula I (or a salt, solvate, or synthetic equivalent thereof), suitably via one or more suitable chemical transformations;
- transforming a synthetic equivalent of the compound of Formula I (or a salt or solvate thereof) into a compound of Formula I (or a salt or solvate thereof), suitably via one or more suitable chemical transformations (e.g. deprotections); and/or
- transforming a synthetic equivalent of a pharmaceutical drug substance as defined herein (or a salt or solvate thereof) into a a pharmaceutical drug substance as defined herein (or a salt or solvate thereof), suitably via one or more suitable chemical transformations (e.g. deprotections).

The method may, following conversion of a compound II to a compound I, thereafter involve transformation of a compound I into another compound of formula I (e.g. by manipulating the relevant substituent groups, e.g. by transforming any one or more of X, Y, $R_1$, $R_2$, or any groups associated therewith, to an alternative one or more of X, Y, $R_1$, $R_2$, or any groups associated therewith). For instance, nitrogen atoms bearing a hydrogen may be derivatised through appropriate coupling with a group other than hydrogen, for instance via glycosylation (e.g. N-glycosylation with a sugar compound or activated sugar to form an N-glycosyl derivative), hemiaminalisation (e.g. N-hemiaminalisation with a lactol or activated lactol to form N-cyclic hemiaminal ethers), N-alkylation, N-acylation, and N-carbamoylation (to form an N-carbamate), and such like. Such transformations are particularly relevant where, for example, a specific compound of Formula I (e.g. flucytosine or a salt or solvate thereof) is further processed to form one of either Capecitabine (where further processing steps suitably involve N-glycosylation at the internal ring NH moiety to form a corresponding N-cyclic hemiaminal ether, and also N-carbamoylation at the external $NH_2$ moiety to form an n-pentyl carbamate) or Emtricitabine (where one of the further processing steps suitably involves N-hemiaminalisation at the internal ring NH moiety to form a corresponding N-cyclic hemiaminal ether).

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The method(s) of the invention may therefore comprise, at any stage (including intermediates) though most suitably after a final synthetic step, optionally, and if necessary:

(a) removing any protecting groups present;
(b) converting the compound Formula I or a pharmaceutical drug substance into another compound of Formula I or another pharmaceutical drug substance; and/or
(c) forming a pharmaceutically acceptable salt thereof.

It will be understood that any of the aforementioned general points regarding the synthesis of a compound of Formula I (or a salt, solvate, or synthetic equivalent thereof) may suitably also apply mutatis mutandis to other compounds and/or methods of the invention, especially those pertaining to a pharmaceutical drug substance (whether that be a compound of Formula I or a derivative thereof).

Manufacture of Compound I and/or Pharmaceutical Drug Substance

The present invention provides a method of manufacturing a compound of Formula I (or a salt, solvate, or synthetic equivalent thereof) as defined herein. Such a method may be termed "electrophilic fluorination", since it suitably involves the electrophilic fluorination (i.e. with an electrophilic fluorinating agent) of a compound of Formula II.

Since the novel method of manufacture affords the desired product in both higher yield and higher purity, particularly in terms of impurities characterised by or derived from the starting material (i.e. compound of Formula II), the present invention also provides a novel compound of Formula I (or a salt, solvate, or synthetic equivalent thereof) obtainable by, obtained by, or directly obtained by the method of manufacturing the compound of Formula I.

Continuous Flow Reactor

The reaction between the compound of Formula II and the electrophilic fluorinating agent is performed in a continuous flow reactor.

The continuous flow reactor is operable (or operated) to mix input materials to thereby produce a reaction mixture and cause a chemical reaction between the input materials. The continuous flow reactor may be simply a reaction vessel (or internal reactor) with input and output flow line(s) (or connectors therefor) into which multiple input loads are continuous fed (and suitably out of which one or more output loads flow), though in the context of the invention the continuous flow reactor may suitably be considered to comprise at least an internal reactor (or reaction vessel) but may additionally comprise any, some, or all other elements of an apparatus for performing the method(s) of the invention (i.e. optionally including any flow lines, connectors, junctions, input reservoirs, output collectors, heating and/or pressure controllers, flow controllers, etc.).

The compound of Formula II and the electrophilic fluorinating agent are collectively "input materials" or are respectively a first and second input material. The product(s) of the reaction are "output materials" (though the output materials may include input materials if there is an incomplete reaction). Suitably a continuous flow reactor is operated to (substantially) continuously mix a first input load (or flow) comprising the compound of Formula II (the first input material) with a second input load (or flow) comprising the electrophilic fluorinating agent (the second input material), suitably so that the respective input materials are mixed together in pre-determined relative quantities, at pre-determinated relative rates, and/or allowed or caused to react together (e.g. through the resulting reaction mixture being exposed to particular pre-determined reaction conditions, or the reaction mixture being otherwise passed through an internal reactor) for a pre-determined time period (i.e. residence time). Suitably the continuous flow reactor is operated to control the relative (and suitably also the absolute) rate of mixing of the relevant input loads. Suitably the input loads each respectively have a known pre-determined concentration of each of the respective input materials. Whereas in a batch process, it is straightforward to determine the relative amounts of the input materials (and by deduction, potentially also the amounts of output materials) by reference to the absolute amounts of material inputted into a batch processing vessel, the relative amounts of input materials (e.g. the relative weight or molar ratios of the first and second input materials) in a continuous flow process, as per the invention, must be established by reference to the concentration of input materials in their respective input loads and the flow rates of these respective input loads. As such, the skilled person is well capable of establishing and/or pre-setting the reaction stoichiometry or relative ratios of input materials of a continuous flow process.

The continuous flow reactor may be any suitable continuous flow reactor, of which there is a variety already well known in the art, for example: pipe/laminar flow systems, falling film reactors, 'counter current' flow reactors, spinning disc devices, pipe-in-pipe systems, and parallel multichannel reactors such as those described in an earlier patent application of the present applicant (WO003/095086), MEPI reactors, and Chemtrix systems. The person skilled in the art is well aware of suitable materials and construction methods for continuous flow reactors, and any suitable materials and construction methods and arrangements may be used. However, continuous flow reactors are often formed from stainless steel, silicon carbide, copper, and such like.

Suitably, the continuous flow reactor comprises two or more fluidly-connected flow line(s) capable of carrying a continuous flow of fluid materials (including input materials and output materials) through the continuous flow reactor. Suitably the continuous flow reactor comprises upstream input flow line(s) (for carrying input loads and materials) fluidly-connected to downstream output flow line(s) (for carrying output loads and materials), suitably via one or more junctions and/or one or more mid-stream flow line(s), and optionally via one or more internal reactor(s).

The continuous flow reactor may comprise any suitable means (or elements) for conveying and mixing the relevant input loads. The continuous flow reactor may be a single integrated apparatus or may comprise two or more pieces of individual apparatus which combine to produce an overall continuous flow apparatus for carrying out the method of the invention. The continuous flow reactor may even include one or more syringes (suitably each associated with a corresponding syringe pump for automatically controlling flow of the relevant input load) and/or one or more mass-flow controllers may be suitable, though more sophisticated equipment is most suitably employed, especially at larger scales. In operation, the continuous flow reactor is also suitably fluidly-connected to distinct reservoirs of relevant input material(s), in order that the relevant input material(s) can become (comprised of the) input loads and duly conveyed through the continuous flow reactor. Suitably one or more pumps (suitably controlled or controllable pumps) are used to pump loads through the continuous flow reactor. Suitably a separate pump is used to control the flow rate of each input load, thereby suitably controlling the relative quantities of each when mixed at a junction.

The continuous flow reactor suitably includes at least a first and second input flow line (suitably each being a suitable tube or pipe for carrying the respective first and second input loads), a first junction (where the first and second flow lines converge, meet or join, and thus by definition downstream from the first and second input flow line(s)), and a first output flow line (suitably a tube or pipe for carrying the relevant output load, suitably resulting from the mixed first and second input loads and optionally further input loads where relevant, and thus by definition downstream from the junction at which said input loads are mixed).

Suitably the first input load comprises (and the first input flow line carries) the compound of Formula II, and the second input load comprises (and the second input flow line carries) the electrophilic fluorinating agent. Suitably, the first and second input lines are respectively fluidly-connected to a first and second reservoir respectively comprising the compound of Formula II (first reservoir) and the electrophilic fluorinating agent (second reservoir). The first and second reservoir suitably each respectively comprise a first input reserve (comprising the first input material/compound of Formula II) and a second input reserve (comprising the second input material/electrophilic fluorinating agent), where suitably each input reserve is in fluid form. Suitably each input reserve comprises pre-determined concentration of the relevant input material. Suitably each fluid reserve equates to each particular input load (i.e. each input load comprises the same concentration of input material as the corresponding input reserve), though optionally further input flow line(s) may carry further (carrier) input load(s) (e.g. diluent(s), carrier(s) for mixing with the relevant input reserves either at or downstream from the respective input reservoirs—this may cause an input load to be more dilute in a given input material than the corresponding input reserve from which it was formed. This may be achieved by locating additional junction(s) upstream from the first junction, i.e. junctions which premix one or more carrier input load(s) with the first and/or second input reserves to produce respective first and/or second input loads. Such additional junction(s) may, for instance, join either or both of the first and/or second input flow line(s) downstream from the first and/or second reservoir(s) but upstream from the first junction, so that each of the first and second input loads are delivered to the first junction (for mixing) with the required concentration of input material(s) in each.

Suitably, as described below, the first input reserve (and/or the first input load), i.e. which contains the compound of Formula II, is provided as a liquid composition comprising the first input material (compound II) mixed with a diluent (i.e. collectively a first input reserve composition). As such, the diluent is suitably a liquid at standard ambient temperature and pressure, though compound II may be a solid. The first input reserve composition is suitably a liquid solution of the compound of Formula II. Suitably the first input load is as high a concentration as possible whilst still remaining fluidly mobile under the operating conditions of the continuous flow reactor. Likewise, therefore, suitably the first input reserve composition is as high a concentration as possible whilst remaining fluidly mobile under said conditions.

Suitably, as described below, the second input reserve (and/or the second input load), i.e. which contains the electrophilic fluorinating agent, is provided as a gaseous composition comprising the second input material (electrophilic fluorinating agent) mixed with a diluent (i.e. collectively a second input reserve composition). As such, the diluent is suitably a gas at standard ambient temperature and pressure, and suitably so is the second input material. The second input reserve composition is suitably a uniform electrophilic fluorinating gaseous composition comprising a mixture of the second input material and a diluent gas. Suitably the concentration of the second input load (with respect to the second input material) is controlled to optimise the reaction condition (e.g. to control exotherms, run-aways, over-heating, etc.). Likewise, therefore, suitably the concentration of the second input reserve composition is duly controlled.

Suitably the continuous flow reactor is operated to carry first and second input loads (respectively comprising compound II and electrophilic fluorinating agent), suitably from respective first and second input reservoirs, via distinct first and second input flow lines, to the first junction, where said input loads are mixed to produce a "reaction mixture". Suitably a separate pump is used to control the flow rate of each input load, to thereby suitably control the relative quantities of each input load (and hence relative quantities of each respective input material) when mixed at the first junction.

To facilitate a chemical reaction between the first and second input materials, the continuous flow reactor suitably comprises an internal reactor (i.e. a first internal reactor), suitably in fluid communication with (or connected to) input and output flow line(s), and is suitably located at or downstream from (and fluidly in-line with) the first junction. Suitably the continuous flow reactor is operable or configured to feed the reaction mixture through the internal reactor (suitably at a pre-determined rate, suitably to provide a pre-determined residence time within the internal reactor). As such, the continuous flow reactor is suitably operated to mix the input loads (i.e. at the junction, either within or upstream from the internal reactor) to form a "reaction mixture" (suitably comprising first and second input materials and/or output material(s) derived from reaction(s) therebetween) which flows through the internal reactor and out of the internal reactor into and through one or more output flow line(s). The internal reactor may be a vessel (like a reactor vessel), tube, or pipe, operable to facilitate reaction of the first and second input materials. In a particular embodiment, the internal reactor is a coiled tube or pipe, suitably with a (substantially) uniform bore or internal diameter. In a particular embodiment, the internal reactor is a standard coiled 1 m long stainless steel tube with an internal diameter of 1.4 mm.

In a particular embodiment, the continuous flow reactor (or collective continuous flow apparatus) includes:
 a first input flow line for carrying the first input load;
 a second input flow line for carrying the second input load,
 a junction at which the first and second input flow lines converge and at which the first and second input loads mix to form a reaction mixture;
 an internal reactor, through which the reaction mixture is configured to flow, located at or downstream from the first junction; and
 a first output flow line for carrying an output load from the internal reactor;
wherein the continuous flow reactor is operated to feed the reaction mixture through the internal reactor.

It will be understood by those skilled in the art that the continuous flow reactor may comprise one or more further input flow lines (i.e. third, fourth, . . . input flow lines), and optionally corresponding one or more further reservoirs (i.e. third, fourth . . . input reservoirs), configured to carry one or more further input loads and/or or input materials (i.e. third, forth, . . . input loads/materials). Additional input loads may be used to modify reaction conditions in real time, or for the delivery of additional reagents or precursors therefor.

The conditions prevailing within the internal reactor may be judiciously selected, controlled, and/or maintained, suitably by controlling one or more reaction parameters (e.g. temperature, pressure, residence time, mixing). The dimensions and shape of the internal reactor may be optionally adjustable, to control one or more reaction parameters. The internal reactor may be (optionally adjustably) dimensioned and/or shaped to provide a desired reaction mixture "residence time" (i.e. the volumetric residence time of the reaction mixture, which is the ratio of the reactor's internal volume and the overall volumetric flow rate of the reaction mixture through the reactor—i.e. where overall volumetric flow rate is suitably the sum of the flow rates of the first and second input loads). Naturally, this "residence time" may also be influenced by the overall flow rate, which may be altered by adjusting the flow rate of the individual input loads. In this context, "residence time" is generally a measure of the duration of reaction within the internal reactor (i.e. the time taken for a given volume of reaction mixture to pass through the reactor). Note, however, that the reaction mixture "residence time" is distinct from the residence time of a given weight, volume, or number of moles, of input and output materials, whose residence times are additionally influenced by the concentration of the relevant materials.

The continuous flow reactor may be operated to induce, adjust, but most preferably maintain one or more reaction parameters within the internal reactor. For instance where the reactor comprises or is associated with a heating or cooling device, the temperature within the internal reactor (and therefore of the reaction mixture) may be selected, maintained, or adjusted—it may be particularly important to apply cooling or otherwise allow heat-exchange to remove heat generated during a reaction by exotherms (this is often the case where fluorine gas reacts with a compound of Formula II). Where the reactor comprises or is associated with a pressure adjusting device (e.g. a vacuum pump or autoclave), the pressure (or lack thereof) within the internal reactor (and therefore of the reaction mixture) may be selected, maintained, or adjusted. Where the reactor comprises an agitation element (e.g. for mixing), mixing of the reaction mixture may be facilitated. Where the reactor is configured to receive input from one or more further input flow lines, prevailing reaction conditions (e.g. pH) within the internal reactor (and therefore of the reaction mixture) may be selected, maintained, or adjusted. Alternatively, where the reactor comprises a gas outlet or gas output flow line (as distinct from a reaction mixture output flow line), optionally connected to a scrubber (e.g. soda lime scrubber for scrubbing excess), gaseous input material(s) and/or gaseous output materials (produced following the chemical reaction) may be conveniently diverted so that an output load (carrying output material(s)) exiting the reactor comprises a reduced concentration of said gaseous materials relative to the concentration of said gaseous materials in the reaction mixture (i.e. within the reactor). Alternatively, however, such separation of gases (and optional scrubbing) may occur downstream from the reactor, suitably at a collector point (where the output load is collected). Such induction, adjustment, and/or maintenance of one or more reaction parameters within the internal reactor may suitably further facilitate a chemical reaction within the internal reactor.

Suitably, once the reaction mixture has passed through the internal reactor, an output load (comprising output materials, which may optionally include one or more of the input materials, though suitably all input materials have reacted within the reactor or been removed from reaction mixture or output load) suitably passes into the one or more output flow line(s) (suitably into a single output line). Suitably the output load is exposed to different conditions (e.g. temperature, heat-exchange, pressure, partial pressure or gaseous input materials) to that of the reaction mixture within the internal reactor. This may be merely due to the cessation of change(s) in the one or more reaction parameters prevailing within the internal reactor. Alternatively, the continuous flow reactor may be operated to induce, adjust, but most preferably maintain one or more parameters within the output flow line(s) (e.g. temperature, pressure, or even a quenching agent to quench a reaction). As such, the reaction is suitably quenched (or at least retarded) following exit from the internal reactor to the output line(s).

Suitably the output load(s) is collected, and suitably thereafter the desired output material(s) are isolated and/or purified therefrom, suitably outside the continuous flow reactor. An output load that has been collected may be termed a "collected output load".

In a particular embodiment, the continuous flow reactor is a microreactor. In a particular embodiment, the continuous flow reactor is a stainless steel tube reactor.

Compounds

The compounds of Formula I and Formula II (shown below) both share common X, Y, $R_1$, $R_2$, groups, each of which may be defined as herein.

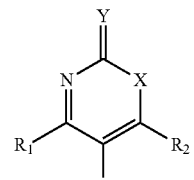

(Formula I)

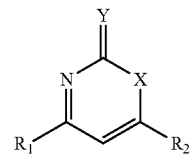

(Formula II)

With regards to particular compounds of the invention (e.g. compound of Formula I or a pharmaceutical drug substance derived therefrom) and particular compounds used (e.g. compound of Formula II) or produced (e.g. compound of Formula I or a pharmaceutical drug substance derived therefrom) by the methods of the invention, or (pharmaceutically acceptable) salts, solvates, or synthetic equivalents thereof: unless otherwise stated, each of X, Y, $R_1$, $R_2$, and any groups associated therewith (e.g. $R_x$, $R_y$, $R_{1a}$, $R_{1b}$, $R_N$, $R_S$, $L_1$, $Q_1$, $R_{L1}$, $R_{L2}$, n) has any of the meanings defined hereinbefore or in any of paragraphs (1) to (26) hereinafter:—

(1) X is $NR_x$; wherein $R_x$ is hydrogen or is independently selected from any $R_N$ group;

(2) X is $NR_x$; wherein $R_x$ is hydrogen or is independently selected from heterocyclyl optionally substituted with one or more $R_S$ groups;

(3) X is $NR_x$; wherein $R_x$ is hydrogen or is a 5-membered heterocyclyl (suitably containing at least one internal oxygen atom and optionally a sulphur atom, though is suitably free of nitrogen atoms) optionally substituted with one or more hydroxyl, (1-3C)alkyl, or (1-3C)alkyl substituted with hydroxy;

(4) X is NR$_x$; wherein R$_x$ is hydrogen or is a 5-membered heterocyclyl group (suitably with only a single internal oxygen heteroatom, or with a single internal oxygen heteroatom and a single internal sulphur heteroatom) optionally substituted with one or more hydroxyl, (1-3C)alkyl, or (1-3C)alkyl substituted with hydroxyl, wherein where R$_x$ is other than hydrogen, R$_x$ forms a hemiaminal ether (or glycosidic) linkage with the nitrogen atom to which it is attached;
(5) X is NH;
(6) Y is O;
(7) R$_1$ is hydrogen or is independently selected from an R$_s$ group selected from amino, (1-8C)alkyl, (1-6C)alkoxy, (1-6C)alkylamino, di-[(1-6C)alkyl]amino, (1-6C)alkoxycarbonyloxy, (2-6C)alkanoyloxy, (2-6C)alkanoylamino, N-(1-6C)alkyl-(2-6C)alkanoylamino, (1-6C)alkoxycarbonylamino, N-(1-6C)alkyl-(1-6C)alkoxycarbonylamino, (1-6C)alkanesulphonylamino and N-(1-6C)alkyl-(1-6C)alkanesulphonylamino, optionally substituted as defined herein;
(8) R$_1$ is an electron donating group (EDG);
(9) R$_1$ is independently selected from NR$_{1a}$R$_{1b}$, OR$_{1a}$, (1-6C)alkoxycarbonylamino, N-(1-6C)alkyl-(1-6C)alkoxycarbonylamino, optionally substituted as defined herein, wherein R$_{1a}$ and R$_{1b}$ are each independently selected from hydrogen or any R$_N$ group as defined herein;
(10) R$_1$ is independently selected from NR$_{1a}$R$_{1b}$ or (1-6C)alkoxycarbonylamino, wherein R$_{1a}$ and R$_{1b}$ are each independently selected from hydrogen or (1-6C)alkyl;
(11) R$_1$ is NH$_2$ or (1-5C)alkoxycarbonylamino;
(12) R$_1$ is NH$_2$;
(13) R$_{1a}$ and R$_{1b}$ are each independently selected from hydrogen or (1-6C)alkyl;
(14) R$_2$ hydrogen;
(15) each R$_N$ group is independently selected from heterocyclyl or formyl independently substituted with one or more R$_s$ groups;
(16) one of R$_N$ (suitably R$_x$) is heterocyclyl substituted with one or more R$_s$ groups;
(17) one of R$_N$ (suitably R$_x$) is 5-membered heterocyclyl substituted with one or more groups selected from hydroxy, (1-8C)alkyl, hydroxy-(1-8C)alkyl, (1-3C)alkoxy-(1-8C)alkyl, or (1-6C)alkoxy;
(18) one of R$_N$ (suitably R$_x$) is 5-membered heterocyclyl substituted with one or more groups selected from hydroxy, (1-3C)alkyl, or hydroxy-(1-3C)alkyl;
(19) one of R$_N$ (suitably R$_x$) is 5-membered heterocyclyl (suitably with a single internal oxygen heteroatom, or with a single internal oxygen heteroatom and a single internal sulphur heteroatom) substituted with one or more groups selected from hydroxy, methyl, or hydroxyethyl; wherein R$_N$ forms a glycosylic (or anomeric) linkage with the nitrogen atom to which it is attached;
(20) one of R$_N$ (suitably one within R$_1$, suitably one of R$_{1a}$ or R$_{1b}$ of a NR$_{1a}$R$_{1b}$ group) is formyl substituted with one or more R$_s$ groups;
(21) one of R$_N$ (suitably one within R$_1$, suitably one of R$_{1a}$ or R$_{1b}$ of a NR$_{1a}$R$_{1b}$ group) is formyl substituted with one or more groups selected from (1-8C)alkyl or (1-6C)alkyl;
(22) one of R$_N$ (suitably one within R$_1$, suitably one of R$_{1a}$ or R$_{1b}$ of a NR$_{1a}$R$_{1b}$ group) is formyl substituted with one or more groups selected from (1-5C)alkyl or (1-5C)alkoxy;
(23) each R$_s$ group is independently selected from halogeno, trifluoromethyl, cyano, isocyano, nitro, hydroxy, mercapto, amino, formyl, carboxy, carbamoyl, ureido, (1-5C)alkyl, (1-5C)alkoxy, (1-4C)alkylthio, (1-4C)alkylamino, di-[(1-4C)alkyl]amino, (1-5C)alkoxycarbonyl, (1-5C)alkoxycarbonyloxy, N-(1-5C)alkylcarbamoyl, N,N-di-[(1-5C)alkyl]carbamoyl, (2-4C)alkanoyl, (2-4C)alkanoyloxy, (2-4C)alkanoylamino, N-(1-5C)alkyl-(2-4C)alkanoylamino, (1-5C)alkoxycarbonylamino, N-(1-5C)alkyl-(1-5C)alkoxycarbonylamino, or from a group of the formula:

L$_1$-Q$_1$ wherein L$_1$ is a direct bond or is selected from CH$_2$, O, S, SO, SO$_2$, N(R$_{L1}$), CO, CR$_{L1}$(O R$_{L2}$), CON(R$_{L1}$), N(R$_{L1}$)CO, N(R$_{L1}$)C(O)O, N(R$_{L1}$)CON(R$_{L2}$), SO$_2$N(R$_{L1}$), N(R$_{L1}$)SO$_2$, OC(R$_{L1}$)$_2$, SC(R$_{L1}$)$_2$ and N(R$_{L1}$)C(R$_{L2}$)$_2$, wherein R$_{L1}$ and R$_{L2}$ are each independently hydrogen or (1-5C)alkyl; and Q$_1$ is (1-5C)alkyl, (2-4C)alkenyl, (2-4C)alkynyl, aryl, aryl-(1-4C)alkyl, (5-6C)cycloalkyl, (5-6C)cycloalkyl-(1-6C)alkyl, heteroaryl, heteroaryl-(1-4C)alkyl, heterocyclyl or heterocyclyl-(1-4C)alkyl; wherein any R$_s$ group is independently optionally further substituted by one or more R$_s$ groups as defined herein (suitably only optionally substituted to the first order level);
(24) each R$_s$ group is independently selected from hydroxy, amino, (1-5C)alkyl, (1-5C)alkoxy, (1-5C)alkoxycarbonylamino; wherein any R$_s$ group is independently optionally further substituted by one or more R$_s$ groups as defined herein (suitably only optionally substituted to the first order level);
(25) each R$_s$ group is independently selected from halogeno, trifluoromethyl, cyano, isocyano, nitro, hydroxy, amino, formyl, carboxy, carbamoyl, ureido, (1-8C)alkyl, (1-6C)alkoxy, (1-6C)alkoxycarbonylamino; wherein any R$_s$ group is independently optionally further substituted by one or more R$_s$ groups (i.e. first order R$_s$ substitutent groups in relation to any given "parent" R$_s$ group), though suitably any first order R$_s$ substituent groups are unsubstituted;
(26) where R$_s$ is optionally substituted with one or more further R$_s$ groups (i.e. by first-order R$_s$ substituents), suitably said further R$_s$ groups are selected from hydroxy, (1-8C)alkyl, hydroxy-(1-8C)alkyl, (1-3C)alkoxy-(1-8C)alkyl, or (1-6C)alkoxy.

In a particular embodiment, the compound(s) of Formula II, I, and/or I-imp are defined as herein, where X is NR$_x$, and Y is O, i.e. the compound(s) respectively have the structural Formula IIa, Ia, and/or Ia-imp shown below:

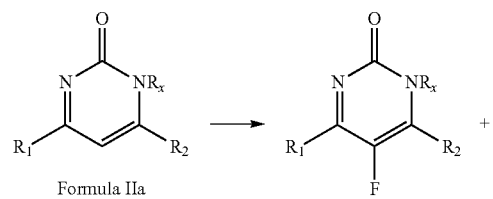

Formula IIa → Formula Ia +

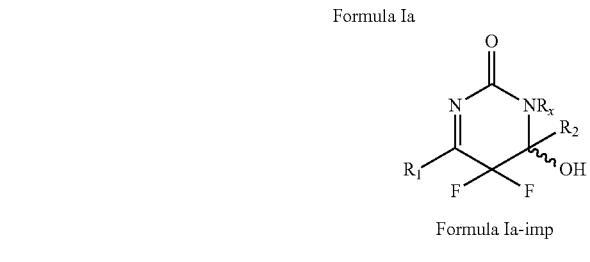

Formula Ia-imp wherein $R_1$, $R_2$, $R_x$, and any groups associated therewith, have any one of the meanings defined herein, or a salt, solvate, or synthetic equivalent thereof.

In a particular embodiment, the compound(s) of Formula IIa, Ia, and/or Ia-imp are defined as herein, where $R_1$ is $NR_{1a}R_{1b}$, i.e. the compound(s) respectively have the structural Formula IIb, Ib, and/or Ib-imp shown below:

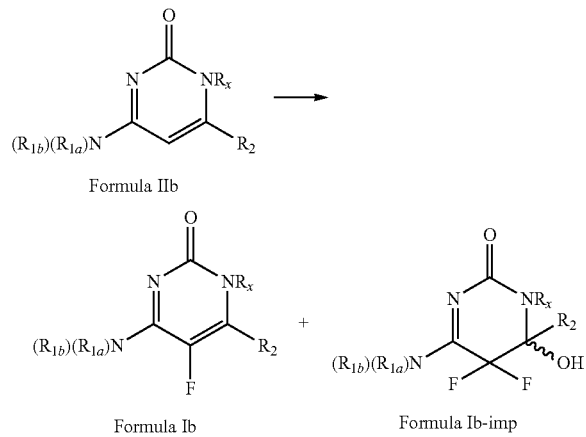

Formula IIb

Formula Ib

Formula Ib-imp wherein $R_{1a}$, $R_{1b}$, $R_2$, $R_x$, and any groups associated therewith, have any one of the meanings defined herein, or a salt, solvate, or synthetic equivalent thereof.

In a particular embodiment, the compound(s) of Formula IIb, Ib, and/or Ib-imp are defined as herein, where $R_1$ is $NH_2$, and $R_2$ is hydrogen, i.e. the compound(s) respectively have the structural Formula IIc, Ic, and/or Ic-imp shown below:

Formula IIc

Formula Ic

Formula Ic-imp wherein $R_x$, and any groups associated therewith, have any one of the meanings defined herein, or a salt, solvate, or synthetic equivalent thereof.

In a particular embodiment, the compound(s) of Formula IIb, Ib, and/or Ib-imp are defined as herein, where $R_x$ and $R_2$ are both hydrogen, i.e. the compound(s) respectively have the structural Formula IId, Id, and/or Id-imp shown below:

Formula IId

Formula Id

Formula Id-imp wherein $R_{1a}$, $R_{1b}$, and any groups associated therewith, have any one of the meanings defined herein, or a salt, solvate, or synthetic equivalent thereof.

In a particular embodiment, the compound(s) of Formula IId, Id, and/or Id-imp are defined as herein, where $R_{1a}$ and $R_{1b}$ are both hydrogen, i.e. the compound(s) respectively have the structural Formula IIe, Ie, and/or Ie-imp shown below:

Formula IIe

Formula Ie

Formula Ie-imp or a salt or solvate. As such, in a particular embodiment, the compound of formula II is cytosine, and the compound of Formula I is flucytosine, or each of these is alternatively a salt or solvate thereof.

In a particular embodiment, the compound of Formula I is selected from flucytosine, emtricitabine, or capecitabine, or a pharmaceutically acceptable salt and/or solvate thereof.

In a particular embodiment, the pharmaceutical drug substance is selected from flucytosine, emtricitabine, or capecitabine, or a pharmaceutically acceptable salt and/or solvate thereof. Compounds, such as emtricitabine or capecitabine may optionally be formed by first forming a different compound of formula I (e.g. flucytosine), and then performing one or more transformation steps to produce emtricitabine or capecitabine.

Electrophilic Fluorinating Agent

The electrophilic fluorinating agent may be any suitable electrophilic fluorinating agent known in the art, though obviously the electrophilic fluorinating agent is suitable for use in a continuous flow reactor. Suitably the electrophilic fluorinating agent is provided as a fluid (whether gaseous or liquid at standard ambient temperature and pressure). The electrophilic fluorinating agent is suitably provided as part of the second input load and/or the second input reserve composition.

Though, in preferred embodiment, the electrophilic fluorinating agent is suitably provided to the continuous flow reactor as (part of) a single input load comprising a (preformed ready-to-use) electrophilic fluorinating agent, in some embodiments the electrophilic fluorinating agent may instead be provided as one or more (more suitably two or more) electrophilic fluorinating agent precursor reagents which suitably react in situ within the continuous flow reactor (suitably in the presence of the compound of Formula II) or in a separate reactor (suitably in the absence of the compound of Formula II) fluidly connected with the continuous flow reactor to form the electrophilic fluorinating agent. As such, references herein to electrophilic fluorinating agent(s) suitably includes any electrophilic fluorinating agent precursor reagent(s) that may ultimately lead to the formation of the electrophilic fluorinating agent (e.g. by reacting two or more electrophilic fluorinating agent precursor reagents). Such electrophilic fluorinating agent precursor reagent(s) may be provided as (part of) a single input load (e.g. with a second input load) or more preferably be provide as (part of) two or more separate input loads (e.g. with second and third input loads). Two or more electrophilic fluorinating agent precursor reagents may suitably constitute separate input materials and be comprised of separate input loads so as to be delivered via two separate input flow lines. As such, the electrophilic fluorinating agent precursor reagents may be provided as second and third input loads—for instance the second input load may comprise gaseous fluorine whilst the third input load may comprise acetic acid, such that the second and third input loads ultimately react to form the electrophilic fluorinating agent acetyl hypofluorite. For the purposes of defining the invention, references herein to a second input load carrying an electrophilic fluorinating agent suitably includes two or more electrophilic fluorinating agent precursor reagents carried as (part of) two or more separate input loads (within two or more separate input flow lines).

Where the electrophilic fluorinating agent is provided as a liquid, suitably it is provided as a solution, suitably in a solvent compatible for use under the reaction conditions. Where the electrophilic fluorinating agent is provided as a liquid, suitably said liquid is (substantially) homogeneous and/or uniform. The electrophilic fluorinating agent itself may be a solid at SATP, but suitably it is used as a solution in an appropriate solvent.

The skilled person will be aware of the wide variety of electrophilic fluorinating agents now available for use in synthetic chemistry, a sample of which include:

Gaseous electrophilic fluorinating agents—fluorine gas, suitably provided as part of an electrophilic fluorinating gaseous composition comprising fluorine and optionally one or more carrier gases (e.g. nitrogen) (i.e. diluted fluorine);

Oxygen-fluorine (O—F) electrophilic fluorinating agents—compounds with an oxygen-fluorine bond, for example: acetyl hypofluorite, cesium fluoroxy sulphate, perchloyl fluoride, bis(fluoroxy)difluoromethane, Fluoroxytrifluoromethane;

Nitrogen-fluorine (N—F) electrophilic fluorinating agents—compounds with a nitrogen-fluorine bond, for example:

N-fluoro-o-benzenedisulfonimide (N FOBS)
N-fluorobenzenesulfonimide (NFSI)
1-Chloromethyl-4-fluoro-1,4-diazoniabicyclo[2.2.2] octane bis(tetrafluoroborate) (Selectfluor™)
2,6-Dichloro-1-fluoropyridinium Trifluoromethanesulfonate
1,1-Difluoro-2,2-bipyridinium
1-Fluoro-2,6-dichloropyridinium Tetrafluoroborate
2-Fluoro-1-methylpyridinium p-Toluenesulfonate
1-Fluoropyridinium Tetrafluoroborate
1-Fluoropyridinium Trifluoromethanesulfonate
1-Fluoro-2,4,6-trimethylpyridinium Tetrafluoroborate
1-Fluoro-2,4,6-trimethylpyridinium Trifluoromethanesulfonate
N-Fluorobenzenesulfonimide
N-Fluoro-N-(chloromethyl)triethylenediamine Bis(tetrafluoroborate)

Suitably, the electrophilic fluorinating agent is provided as part of the second input load (or as part of the second input reserve composition). Suitably the second input load (or as part of the second input reserve composition) comprises an electrophilic fluorinating agent in a concentration suitable for reaction. Given that the second input reserve composition and/or second input load may be in gas or liquid form, the concentration of the electrophilic fluorinating agent within the second input reserve composition and/or second input load may be given in one or more of molarity, wt %, mol %, or partial pressure.

Suitably the second input reserve composition (and/or second input load) comprises the electrophilic fluorinating agent in a concentration between 1 wt % and 30 wt %, suitably between 2 wt % and 20 wt %, suitably between 5 wt % and 15 wt %, most suitably about 10 wt %.

Suitably the second input reserve composition (and/or second input load) comprises between 1 and 30 mol % electrophilic fluorinating agent, suitably between 2 and 20 mol %, suitably between 5 and 15 mol %, most suitably about 10 mol %.

Where the electrophilic fluorinating agent (e.g. fluorine) and the second input reserve composition (and second input load) are gaseous, suitably the second input reserve composition (and/or second input load) comprises between 1 and 30% electrophilic fluorinating agent, suitably between 2 and 25%, suitably between 3 and 20%, suitably between 5 and 15%, more suitably between 8 and 12% electrophilic fluorinating agent, most suitably about 10% electrophilic fluorinating agent. Suitably the balance of ingredients in the the second input reserve composition (and second input load) (i.e. up to 100%) is constituted by the one or more carrier gas(es), suitably nitrogen. In a particular embodiment, the electrophilic fluorinating gaseous composition comprises or consists essentially of 5 to 15% electrophilic fluorinating agent and 85 to 95% diluent gas(es). These percentages may be by moles, by weight, or by volume.

In a preferred embodiment, the electrophilic fluorinating agent is a gaseous electrophilic fluorinating agent. Suitably the electrophilic fluorinating agent is fluorine gas, optionally provided as an electrophilic fluorinating gaseous composition (i.e. corresponding to the second input load and/or second input reserve composition) comprising fluorine and optionally one or more carrier gases (e.g. nitrogen). Any carrier gases are suitably inert gases, suitably inert to fluorine and suitably also inert to any other starting materials, products, or reagents of the methods of the invention. Suitably, the electrophilic fluorinating agent is fluorine gas provided as an electrophilic fluorinating gaseous composition comprising or consisting essential of fluorine and nitrogen. In a particular embodiment, an electrophilic fluorinating gaseous composition comprises between 1 and 30% fluorine, suitably between 2 and 25% fluorine, suitably between 3 and 20% fluorine, suitably between 5 and 15% fluorine, more suitably between 8 and 12% fluorine, most suitably about 10% fluorine. Suitably the balance of ingredients in the electrophilic fluorinating gaseous composition (i.e. up to 100%) is constituted by the one or more carrier gas(es), suitably nitrogen. In a particular embodiment, the electrophilic fluorinating gaseous composition comprises or consists essentially of 5 to 15% fluorine and 85 to 95% nitrogen, most suitably 10% fluorine and 90% nitrogen, where % values are by volume (though since such gaseous systems behave substantially as an ideal gas, the % values may also be by weight).

An electrophilic fluorinating gaseous composition is suitably provided to a reaction mixture as a constant flow.

Acid/Diluent for Compound of Formula II

In methods of the invention, the compound of Formula II is suitably provided as part of a first input reserve composition (or a first input load, which may be the same or different to the first input reserve composition, preferably the same) comprising the compound of Formula II and one or more diluent(s) (i.e. a diluent system). Most suitably, the first input reserve composition (and/or the first input load) is a solution of compound II. Suitably the first input reserve composition comprises compound II in a concentration between 0.01M and 10M, suitably 0.1M to 3M, suitably 0.5M to 1.5M, most suitably about 1M. However, most suitably it is the first input load that comprises compound II in a concentration between 0.01M and 10M, suitably 0.1M to 3M, suitably 0.5M to 1.5M, most suitably about 1M. As such, though the input load is most suitably (substantially) the same as the first input reserve composition (i.e. the form of the first input material taken from the reservoir thereof), if they are different then suitably a more concentrated first input reserve composition is diluted during operation of the continuous flow reactor so that the respective input load has the required concentration.

Suitably the first input reserve composition comprises compound II in a concentration between 1 wt % and 20 wt %, suitably between 5 wt % and 15 wt %, suitably between 7 wt % and 10 wt %, most suitably about 9 wt %. However, most suitably it is the first input load that comprises compound II in a concentration between 1 wt % and 20 wt %, suitably between 5 wt % and 15 wt %, suitably between 7 wt % and 10 wt %, most suitably about 9 wt %.

Suitably the first input reserve composition (and/or first input load) comprises compound II in a concentration between 0.001 and 1.0 mol %, suitably between 0.01 and 0.5 mol %, most suitably between 0.02 and 0.6 mol %.

The diluent system suitably comprises an acid. Suitably the acid has a $pK_a$ greater than or equal to 2.0, suitably greater than or equal to 3.0, suitably greater than or equal to 3.17 (i.e. greater than or equal to the $pK_a$ of hydrofluoric acid), suitably greater than or equal to 3.5. Suitably the acid has a $pK_a$ less than or equal to 5.0, suitably less than or equal to 4.0, suitably less than or equal to 3.8. Most suitably, the acid has a $pK_a$ of about 3.77.

Suitably the acid is an organic acid, suitably a carboxylic acid. Suitably the carboxylic acid is a liquid at SATP. The carboxylic acid is suitably defined by $R'CO_2H$, wherein R' is (1-8C)alkyl, (2-8C)alkenyl, or (2-8C)alkynyl, optionally substituted by one or more halogeno (especially fluoro), trifluoromethyl, cyano, isocyano, nitro, hydroxy, mercapto, or (1-6C)alkoxy. In an embodiment, R' is (1-8C)alkyl optionally substituted by one or more halogeno (especially fluoro). In an embodiment, R' is (1-3C)alkyl optionally substituted by one or more fluoro. In an embodiment, the carboxylic acid is selected from formic acid, acetic acid, propanoic acid, trifluoroacetic acid, or trichloroacetic acid. Most preferably, the acid is formic acid.

The diluent system may comprise the acid and one or more additional solvents. However, suitably the diluent system comprises at least 20 wt % acid, suitably at least 40 wt %, suitably at last 60 wt %, more suitably at least 80 wt %, and most suitably the diluent system consists of or consists essentially of the acid. As such, in a preferred embodiment, the diluent is formic acid. However, diluents, such as methanol and/or acetonitrile maybe used.

It will be understood that the acid may optionally be provided as (part of) a separate input load to the compound of Formula II, though most suitably they are part of the same input load.

Reaction Conditions

The reaction between the compound of Formula II and the electrophilic fluorinating agent (which may be abbreviated to "the fluorination reaction") may be further defined by reference to one or more reaction conditions.

One of the reaction conditions may be the relative amounts of the input materials within a reaction mixture (or fed into the reaction mixture), suitably the relative amounts of compound II and electrophilic fluorinating agent. Suitably, the molar ratio of electrophilic fluorinating agent to compound II is greater than or equal to 1:1 (i.e. suitably at least 1 mole electrophilic fluorinating agent per mole of compound II), suitably greater than or equal to 1.1:1, suitably greater than or equal to 1.2:1, suitably greater than or equal to 1.4:1. Suitably, the molar ratio of electrophilic fluorinating agent to compound II is less than or equal to 2:1 (i.e. suitably at most 1 mole electrophilic fluorinating agent per mole of compound II), suitably less than or equal to 1.8:1, suitably less than or equal to 1.6:1, suitably less than or equal to 1.4:1. In a particular embodiment, the molar ratio of electrophilic fluorinating agent to compound II is about 1.25:1 (especially at larger scale). In a particular embodiment, the molar ratio of electrophilic fluorinating agent to compound II is about 1.5:1. Most suitably the molar ratio of electrophilic fluorinating agent to compound II is between 1.2:1 and 1.6:1.

Another one of the reaction conditions may be the absolute concentrations of the input materials.

The concentration of the compound of Formula II in the first input load (and suitably also within the first input reserve) is between 0.01M and 10M, between 1-20 wt %, or between 0.001-1.0 mol %.

The concentration of the electrophilic fluorinating agent in the second input load (and suitably also within the second input reserve) is suitably between 1-30 wt %, or between 1 and 30 mol %, or between 1 and 30% by volume. Suitably the second input load (and second input reserve) is a gas mixture, suitably a mixture of fluorine and nitrogen.

Another one of the reaction conditions may be the relative flow rates of the input loads and/or input reserve compositions. Knowing the relative flow rates of, for instance the first and second input loads (compound II and electrophilic fluorinating agent), and also the absolute concentrations of the first input material (compound II) in the first input load and second input material (electrophilic fluorinating agent) in the second input load, allows for the relative amounts (in weight or moles) and also overall absolute molar concentrations of the input materials in a reaction mixture. Knowing the relative amounts of input materials provides an indication of the relative equivalents of each (or stoichiometry), which may be kinetically or thermodynamically influential. Knowing the overall absolute molar concentrations of the input materials in the reaction mixture allows for an evaluation of kinetics, since the concentration of the reaction may effect reaction rate and thus the residence time required for the reaction to proceed to a certain point (preferably completion).

Suitably, flow rates of the first input load and second input load may be given in terms of volumetric flow rate (flow volume per unit time), but also in terms of molar flow rate (moles of relevant input material per unit time). However, their relative flow rates may be given as a ratio. As such, the relative volumetric flow rate may be volumetric flow rate of the first input load divided by volumetric flow rate of the second input load. The relative molar flow rate may be molar flow rate of the first input material divided by molar flow rate of the second input material.

Suitably, the relative volumetric flow rate of the first input load relative to the second input load (first input load flow rate/second input load flow rate) is between 0.0001 and 0.1, suitably between 0.0005 and 0.01, suitably between 0.001 and 0.005, most suitably about 0.00333333. For instance, where 1M formic acid solution of cytosine (first input load) flows through the continuous flow reactor at a flow rate of 4 mL/hr such that cytosine is fluorinated with a gaseous mixture comprising 10 mol % fluorine in nitrogen (second input load) flowing at a flow rate of 20 mL/min, the relative volumetric flow rate is 0.0033 (i.e. the second input load has a volumetric flow rate approximately 300 times higher than the first input load).

Suitably, the relative molar flow rate of the first input load (or first input material) relative to the second input load (or second input material) (first input load flow rate/second input load flow rate) is between 0.5 and 1, suitably between 0.6 and 0.9, suitably between 0.625 and 0.83333, suitably about 0.8. For instance, a 1M formic acid solution of cytosine (first input load) flowing at 4 mL/hr equates to 4 mmol/hr, and a gaseous mixture comprising 10 mol % fluorine in nitrogen (second input load) flowing at 20 mL/min equates to 5 mmol/hr. As such, the relative molar flow rate is 0.8 (i.e. the second input material has a molar flow rate approximately 1.25 times higher than the first input material—this equates to a reaction mixture comprising 1.25 moles of second input material per mole of first input material). As such, relative molar flow rates equate to molar ratios, and is thus a very important parameter.

Another one of the reaction conditions may be the overall flow rate—i.e. the combined flow rate of both input loads and/or input reserve compositions (or the flow rate of the reaction mixture, which is suitably formed by mixing the first and second input loads). This is perhaps a more important parameter from a chemical engineering point of view, since the overall flow rate generally dictates the residence time required in order to maintain a particular quality of output load/materials. This in turn may effect how the continuous flow reactor is adapted (e.g. the size or internal volume of an internal reactor). This is particular important for scale-up, especially where output rates are desirably increased.

Like relative flow rates, overall flow rates may be given in terms of overall volumetric flow rate (flow volume of combined input loads per unit time, or flow volume of the reaction mixture per unit time) or overall molar flow rate (combined number of moles of both input materials flowing per unit time).

Suitably, the overall volumetric flow rate of the first and second loads (first input load flow rate+second input load flow rate) is between 100 mL/hr and 10,000 L/hr, suitably between 500 mL/hr and 10 L/hr, suitably between 1000 mL/hr and 1500 mL/hr, most suitably about 1204 mL/hr.

Suitably, the overall molar flow rate of the first and second materials (first input material flow rate+second input material flow rate) 9 mmol/hr is between 0.1 mmol/hr and 75 mol/hr, suitably between 1 mmol/hr and 75 mmol/hr, suitably between 5 mmol/hr and 15 mmol/hr, most suitably about 9 mmol/hr.

However, it will be appreciated that the skilled person may scale-up this continuous flow fluorination process as desired, and thus the overall volumetric and molar flows will change accordingly.

Another one of the reaction conditions may be the reactor volume itself, and potentially also the shape of the reactor. As will become apparent, for a given output there is generally a relationship between the reactor volume and overall flow rate. Suitably, all other things being equal, a reactor's output (e.g. the quality of the output load in terms of the distribution of output materials therein) may be kept (substantially) constant if the residence time (discussed below) is kept (substantially) constant. This means, if overall flow rate is increased, the internal reactor volume should also be increased proportionally in order to maintain the same residence time.

Another one of the reaction conditions may be the residence time (herein a volumetric residence time) of the reaction mixture (i.e. after the first and second input loads are mixed together). The residence time is a function of the internal volume of a region within the continuous flow reactor during which a reaction between the first and second input materials occurs (which is suitably the internal volume of the or an internal reactor) and the overall volumetric flow rate of the reaction mixture (or combined input loads). Residence time may be summarised as:

$$\text{Residence time } (T_r) = \text{Internal Reactor Volume } (V_r) / \text{Overall Volumetric Flow Rate } (F_o);$$

or $$T_r = V_r / F_o$$

wherein $T_r$ is given in units of time, $V_r$ is given in units of volume, and $F_o$ is given in units of volume per unit time.

The residence time of the reaction mixture (volume of reactor/overall volumetric flow rate of reaction mixture) is suitably between 0.1 seconds and 120 seconds, suitably between 0.5 seconds and 60 seconds, suitably between 1 second and 10 seconds, suitably between 3 and 7 seconds, most suitably about 4.6 seconds.

However, in certain systems, for instance, where a fluorine gas composition is used as the electrophilic fluorinating agent, one may consider only the residence time of the liquid phase. In such cases, an "overall volumetric flow rate" ($F_o$) may be replaced in the above equation with the "liquid volumetric flow rate" ($F_l$) to give the residence time of the liquid. Clearly $F_l$ will generally be much lower than $F_o$ and so residence times will be correspondingly higher. References in the example section to "residence time" refers to the residence time of the liquid phase only, hence the long residence times being quoted.

As such, suitably any scale-up of the continuous flow reaction would maintain the residence time within this range, all other things being equal.

Another one of the reaction conditions may be the temperature, or the application of heating or cooling. In some of the methods of the invention, the continuous flow reactor is suitably operated to heat the internal reactor to facilitate the reaction. However, in preferred embodiments, the continuous flow reactor is operated to cool the internal reactor (or at least allow heat exchange to remove excess heat from inside the reactor), especially where the reaction is exothermic.

Clearly the skilled person will now be capable of adjusting various parameters to optimise the fluorination reaction for a given compound of Formula II and a given electrophilic fluorinating agent.

Post-reaction/Output Materials/Output Load/Product

An output from the reaction (or output from the internal reactor) is suitably termed an "output load". Features and definitions stipulated herein in relation to any particular output load may refer to an output load at any point along a corresponding output flow line (including immediately on exit from an internal reactor) and/or may include a "collected output load" where the relevant output load is collected. It will be appreciated, however, that a collected output load may have a different composition than the output load exiting an internal reactor in cases where the output load is modified along the corresponding output flow line (e.g. with quenching, scrubbing etc.) or at the collector point itself (e.g. if a gaseous component is removed and optionally scrubbed). However, the present invention does not exclude where an output load is itself subjected to further manipulation or alteration (e.g. further reactions, whether the same or different from a first reaction in a first internal reactor—a first output load may enter a second internal reactor where it may be treated with one or more additional input materials and thereafter exit as a second output load; or post-reaction treatments such as quenching, scrubbing, etc.) before the final output load is ultimately collected as the collected output load.

As depicted in Scheme 1, the output load of the continuous flow reactor may comprise (or the output material(s) may include) a compound of Formula I (the desired product) and a compound of Formula I-imp (a difluorinated contaminant). However, additionally the output load may comprise (or the output material(s) may include) one or more input material(s), depending on the circumstances. For instance, if the electrophililic fluorination reaction is incomplete (e.g. if insufficient equivalents of electrophilic fluorinating agent were used, if residence time in the internal reactor was insufficient, if conditions within the internal reactor were inadequate), the output load may comprise (or the output material(s) may include) the compound of Formula II. However, suitably the reaction conditions (e.g. relative amounts of input materials) and reaction parameters (e.g. residence time and shape/dimensions of internal reactor) drive the electrophilic fluorination reaction (substantially) to completion, and thus suitably the output load (and output materials) are (substantially) free of the compound of Formula II.

In a particular embodiment, the output load (or the output material(s)—i.e. passing through the output flow line) comprise:
  100 parts by moles compound of Formula I
  0.1-30 parts by moles compound of Formula I-imp
  0-10 parts by moles compound of Formula II.

In a particular embodiment, the output load comprises (or the output material(s)—i.e. passing through the output flow line) comprise:
  100 parts by moles compound of Formula I
  1-20 parts by moles compound of Formula I-imp
  0.1-5 parts by moles compound of Formula II.

In a particular embodiment, the output load (or the output material(s)—i.e. passing through the output flow line) comprise:
  100 parts by moles compound of Formula I
  2-10 parts by moles compound of Formula I-imp
  0.5-2 parts by moles compound of Formula II.

In a particular embodiment, the output load (or the output material(s)—i.e. passing through the output flow line) comprise:
  about 99 parts by moles compound of Formula I
  about 5 parts by moles compound of Formula I-imp
  about 1 parts by moles compound of Formula II;
  which may be alternatively expressed as a molar ratio of 99:5:1 of compound of Formula I, compound of Formula I-imp, and compound of Formula II respectively.

In a particular embodiment, the output load (or the output material(s)—i.e. passing through the output flow line) comprise:
  100 parts by moles compound of Formula I
  0.1-30 parts by moles compound of Formula I-imp In a particular embodiment, the output load (or the output material(s)—i.e. passing through the output flow line) comprise:
  100 parts by moles compound of Formula I
  1-20 parts by moles compound of Formula I-imp In a particular embodiment, the output load (or the output material(s)—i.e. passing through the output flow line) comprise:
  100 parts by moles compound of Formula I
  2-10 parts by moles compound of Formula I-imp In a particular embodiment, the output load (or the output material(s)—i.e. passing through the output flow line) comprise:
  about 99 parts by moles compound of Formula I
  about 5 parts by moles compound of Formula I-imp
  which may be alternatively expressed as a molar ratio of 99:5 of compound of Formula I and compound of Formula I-imp respectively.

Here we have ignored any gaseous output materials, which may in any case be suitably removed from (e.g. or scrubbed out) of the output load of the continuous flow reactor, be it in an internal reactor, at a point downstream from the internal reactor (e.g. along the output flow line(s)), or at the ultimate output load collection point.

Suitably the above embodiments relate to the collected output load, which is suitably collected within or from the continuous flow reactor in any suitable vessel. In a particular embodiment, the output load is collected in a vessel associated with a scrubber (e.g. soda lime), suitably to "scrub out" excess fluorine gas.

The components of the output load may be analysed by methods well known in the art or by methods illustrated in the accompanying Examples. For instance, the output load may be examined by NMR (e.g. $^1$H and/or $^{19}$F NMR, hplc, LC-MS, etc.).

The collected output load (or even an uncollected output load) may be further reacted (suitably as defined herein—e.g. to further transform the compound of Formula I into either another compound of Formula I or a or an alternative pharmaceutical drug substance), either directly without post-reaction processing (e.g. workup, purification, isolation, etc.) or following post-reaction processing.

In preferred embodiments, the collected output load is isolated and/or purified, either partially or fully, to yield a purified product (whether partial or fully) using techniques well known in the art. Most suitably the collected output load is first concentrated in vacuo. The concentrated collected output load is then suitably recrystallised (suitably from water), to produce product crystals (i.e. a compound of Formula I or composition thereof). The product crystals are suitably filtered and dried.

The purified product suitably comprises the compound of Formula I. The purified product is suitably (substantially) free of the compound of Formula I-imp. The purified product is suitably (substantially) free of the compound of Formula II.

In a particular embodiment, the purified product comprises:
  100 parts by moles compound of Formula I
  0-2 parts by moles compound of Formula I-imp
  0-2 parts by moles compound of Formula II.

In a particular embodiment, the purified product comprises:
  100 parts by moles compound of Formula I
  0-1 parts by moles compound of Formula I-imp
  0-1 parts by moles compound of Formula II.

In a particular embodiment, the purified product comprises:
  100 parts by moles compound of Formula I
  0-0.1 parts by moles compound of Formula I-imp
  0-0.1 parts by moles compound of Formula II.

Suitably the molar yield of the purified product (by reference to the quantity of input material compound of Formula II) is greater than or equal to 40%, suitably greater than or equal to 50%, suitably greater than or equal to 60%.

Pharmaceutical Drug Substance(s)

The compound of Formula I, whether part of an output load (collected or uncollected), a partially isolated or partially purified output load or product, or a purified product, may itself be a pharmaceutical drug substance as defined herein (e.g. especially where cytosine is fluorinated to yield flucytosine, or where relevant moieties have been pre-installed prior to the electrophilic fluorination method of the invention, as may be the case for emtricitabine or capecitabine) or may be further transformed into a or a different pharmaceutical drug substance (e.g. emtricitabine, capecitabine). Further transformation step or steps would be routine to those skilled in the art, particularly in relation to emtricitabine and capecitabine where there exists a body of literature describing their respective syntheses. The skilled person following the teachings outlined in the present disclosure would now find it straightforward to replace fluorination steps in the known syntheses with the electrophilic fluorination method of the invention.

As such, the present invention provides a method of manufacturing a pharmaceutical drug substance, or a pharmaceutically acceptable salt or solvate thereof, the method comprising:
  manufacturing a compound of Formula I (especially flucytosine), or a salt or solvate thereof, by the method as defined herein;
  optionally thereafter performing one or more further step or steps to produce the pharmaceutical drug substance (or a pharmaceutically acceptable salt, solvate, or synthetic equivalent thereof);
  optionally transforming a synthetic equivalent of the pharmaceutical drug substance (or a salt or solvate thereof) into a pharmaceutical drug substance (or a salt or solvate thereof) via one or more suitable chemical transformations (e.g. deprotections);
  optionally, and if necessary:
  (a) removing any protecting groups present;
  (b) converting the pharmaceutical drug substance into a different pharmaceutical drug substance; and/or
  (c) forming a pharmaceutically acceptable salt thereof.

By way of Example, emtricitabine may be synthesised by preparing flucytosine in accordance with the method of the invention, and thereafter N-coupling flucytosine (or a synthetic equivalent thereof—e.g. silylated flucytosine) with the relevant group(s) or compound(s), in this case a lactol (or synthetic equivalent thereof—e.g. acetylated lactol). WO 92/14743 illustrates the relevant steps from flucytosine to emtricitabine, whereby flucytosine is nucleophilically activated (by silylation) and reacted with an electrophilically activated lactol (e.g. O-butyryl-protected acetyl-activated lactol) under appropriate conditions (e.g. lewis acidic conditions, e.g. $SnCl_4$) to produce emtricitabine or a protected form thereof (e.g. O-butyryl-protected) which may be finally deprotected (e.g. using basic conditions) to yield emtricitabine. Finally the emtricitabine is suitably resolved and/or a suitable pharmaceutically acceptable salt formed.

In an embodiment, the method of manufacturing a pharmaceutical drug substance (especially emtricitabine) comprises:
  manufacturing flucytosine, or a salt or solvate thereof, by the method as defined herein;
  N-coupling flucytosine, via an internal ring nitrogen (NH) thereof, with a lactol (2-(hydroxymethyl)-1,3-oxathiolan-5-ol) to form a corresponding N-cyclic hemiaminal ether, suitably by reacting flucytosine or a derivative thereof (e.g. O-silylated flucytosine) with a lactol (2-(hydroxymethyl)-1,3-oxathiolan-5-ol) or a derivative thereof (e.g. anomerically-activated hemiacetal and/or protected primary alcohol), suitably under acidic or lewis acidic (e.g. $SnCl_4$) conditions;
  and optionally, and if necessary:
  (a) removing any protecting groups present;
  (b) forming a pharmaceutically acceptable salt thereof.

Likewise, capecitabine may be synthesised by preparing flucytosine in accordance with the method of the invention, and thereafter derivatising both derivatisable nitrogen atoms of flucytosine by N-coupling flucytosine (or a synthetic equivalent thereof—e.g. again in this case silylated flucytosine is suitable) with the relevant group(s) or compound (s), in this case a lactol (or synthetic equivalent thereof—e.g. acetylated lactol). U.S. Pat. No. 5,453,497 illustrates the relevant steps from flucytosine to capecitabine, whereby flucytosine is silylated and then reacted with an electrophilically activated lactol (e.g. O-acetyl-protected acetyl-activated lactol) under appropriate conditions (e.g. lewis acidic conditions, e.g. $SnCl_4$) to produce an intermediate compound which is then suitably further N-coupled (this time upon the free external $NH_2$ moiety) to an appropriate alkyloxycarbonyl group (e.g. n-pentyloxycarbonylchloride) to produce capecitabine or a protected form thereof (e.g. O-acetyl-protected) which may be finally deprotected (e.g. using basic conditions) to yield capecitabine. Finally the capecitabine is suitably resolved and/or a suitable pharmaceutically acceptable salt formed.

In an embodiment, the method of manufacturing a pharmaceutical drug substance (especially capecitabine) comprises:
  manufacturing flucytosine, or a salt or solvate thereof, by the method as defined herein;
  N-coupling flucytosine (or the corresponding carbamate—see below), via an internal ring nitrogen (NH) thereof, with a lactol (5-methyltetrahydrofuran-2,3,4-triol) to form a corresponding N-cyclic hemiaminal ether, suitably by reacting flucytosine or a derivative thereof (e.g. O-silylated flucytosine) with a lactol ((3R,4S,5R)-5-methyltetrahydrofuran-2,3,4-triol or 5-methyltetrahydrofuran-2,3,4-triol) or a derivative thereof (e.g. anomerically-activated hemiacetal and/or protected alcohols), suitably under acidic or lewis acidic (e.g. $SnCl_4$) conditions;

N-coupling flucytosine or the N-cyclic hemiaminal ether, via an external nitrogen ($NH_2$) thereof, to a n-pentoxycarbonyl group to form a corresponding carbamate, suitably by reacting flucytosine (or a derivative thereof) or the N-cyclic hemiaminal ether with n-pentoxycarbonic acid or a synthetic or activated derivative thereof (e.g. n-pentoxycarbonylchloride or n-pentanol in conjunction with the corresponding isocyanate of flucytosine or the N-cyclic hemiaminal ether);

and optionally, and if necessary:
(a) removing any protecting groups present;
(b) forming a pharmaceutically acceptable salt thereof.

As such, the present invention provides a method of manufacturing a pharmaceutical drug substance (or a pharmaceutically acceptable salt, solvate, or synthetic equivalent thereof) as defined herein, optionally involving performing one or more further step or steps after the electrophilic fluorination reaction to produce the pharmaceutical drug substance (or a pharmaceutically acceptable salt, solvate, or synthetic equivalent thereof), suitably coupling steps and optional deprotection steps. Such pharmaceutical drug substances suitably comprise a core or derivative of the compound of Formula I.

Specific Embodiment

In a particular embodiment, the compound of Formula I is flucytosine or a salt or solvate thereof, the compound of Formula II is cytosine (suitably provided as a first input load comprising a solution of cytosine, suitably an organic acid solution thereof), the electrophilic fluorinating agent is fluorine (suitably provided as a second input load comprising fluorine and nitrogen); wherein the cytosine and fluorine are provided to the reaction mixture so that the initial molar ratio of fluorine to cytosine is between 1.2:1 and 1.6:1 (suitably a relative molar flow rate of cytosine to fluorine between 0.625 and 0.833330); wherein the residence time of the reaction mixture is suitably between 1 second and 10 seconds.

In a particular embodiment, flucytosine (or salt or solvate thereof) formed by the method of the invention may be or otherwise be transformed into a pharmaceutical drug substance (or pharmaceutically acceptable salt or solvate thereof). The pharmaceutical drug substance is suitably selected from emtricitabine and capecitabine, and suitably transforming flucytosine (or salt or solvate thereof) into emtricitabine or capecitabine (or a pharmaceutically acceptable salt or solvate thereof) may involve performing one or more transformation steps. The one or more transformation steps may involve N-coupling flucytosine (or a synthetic equivalent thereof—e.g. a silylated derivative of flucytosine) with the relevant group or groups or with the relevant compound or compounds (e.g. activated lactol and optionally also an activated alkylcarbonic acid) and optionally thereafter, and where necessary, performing a deprotection and/or resolution to afford the desired pharmaceutical drug substance(s).

The novel fluorination methods of the invention can significantly improve the manufacturing process of the relevant pharmaceutical drug substance(s) and suitably improves the quality of the pharmaceutical drug substance(s).

Pharmaceutical Compositions

The invention provides formulations comprising a pharmaceutical drug substance (or pharmaceutically acceptable salt or solvate thereof) as defined herein formulated for pharmaceutical use and optionally further comprising a pharmaceutically acceptable diluent, excipient and/or carrier.

The invention therefore includes pharmaceutical formulations which may include, in addition to active ingredient, a pharmaceutically acceptable diluent, excipient and/or carrier. Such formulations may be used in the methods of the disclosure. Additionally or alternatively, pharmaceutical formulations may include a buffer, stabiliser and/or other material well known to those skilled in the art. Such materials should be non-toxic and should not interfere with the efficacy of the active ingredient. The precise nature of the carrier or other material will depend on the route of administration, which may be any suitable route, for example by a parenteral route and particularly by infusion or injection (with or without a needle). The route of administration may be subcutaneous injection. The route of administration may be intravenous injection or infusion. Other routes of administration which may be used include administration by inhalation or intranasal administration.

Compositions are provided that include one or more of the actives that are disclosed herein in a carrier. The compositions can be prepared in unit dosage form for administration to a subject. The amount and timing of administration are at the discretion of the treating physician to achieve the desired purposes. The active may be formulated for systemic or local administration. In one example, the active formulated for parenteral administration, such as subcutaneous or intravenous administration.

For parenteral administration, the active can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilised, e.g. by known or suitable techniques.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Vehicles for injection can be a non-toxic diluting agent such as aqueous solution or a sterile injectable liquid. As the usable vehicle or solvent, water, Ringer's solution, isotonic saline, etc. are allowed; as a solvent or suspending liquid, a sterile non-volatile oil can be used. For these purposes, any kind of non-volatile oil may be used, including natural or synthetic or semisynthetic fatty oils or fatty acids; natural or synthetic or semisynthetic mono- or di- or tri-glycerides.

The compositions for administration, therefore, can include a solution of the active dissolved in a pharmaceutically acceptable carrier, such as an aqueous carrier. A variety of aqueous carriers can be used, e.g., buffered saline. These solutions are sterile and generally free of undesirable matter. These compositions may be sterilised by conventional, well known sterilisation techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride and/or sodium lactate. The concentration of active in these formulations can vary widely, and may be selected based on fluid volumes, viscosities and/or body weight in accordance with the particular mode of administration selected and the subject's needs.

A typical pharmaceutical composition for intravenous or subcutaneous administration includes about 0.1 to 10 mg of active per subject per day. Actual methods for preparing administrable compositions, whether for intravenous or subcutaneous administration or otherwise, will be known or apparent to those skilled in the art and are described in more detail in such publications as Remington's Pharmaceutical Science, 19th ed., Mack Publishing Company, Easton, Pa. (1995).

The active may be provided in lyophilised form and rehydrated, e.g. with sterile water or saline, before administration, although actives may be provided in sterile solutions of known concentration. The active solution may then be added to an infusion bag containing 0.9% sodium chloride, USP, and typically administered at a dosage of from 0.5 to 15 mg/kg of body weight.

Amounts effective for therapeutic use, which may be a prophylactic use, will depend upon the severity of the disease and the general state of the patient's health. A therapeutically effective amount of the active is that which provides either subjective relief of a symptom(s) or an objectively identifiable improvement as noted by the clinician or other qualified observer.

An active of the disclosure may be administered in conjunction with another active agent, whether simultaneously, separately or sequentially. The other active agent may be a second active agent of the invention or an active agent falling outside the invention.

Single or multiple administrations of the formulations of the disclosure are administered depending on the dosage and frequency as required and tolerated by the patient. In any event, the composition should provide a sufficient quantity of at least one of the actives disclosed herein to effectively treat the patient, bearing in mind though that it may not be possible to achieve effective treatment in every instance. The dosage can be administered once but may be applied periodically until either a therapeutic result is achieved or until side effects warrant discontinuation of treatment. The dose may be sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., Therapeutic Peptides and Proteins: Formulation, Processing, and Delivery Systems, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., Colloidal Drug Delivery Systems, J. Kreuter, ed., Marcel Dekker, Inc., New York, N.Y., pp. 219-342 (1994); and Tice & Tabibi, Treatise on Controlled Drug Delivery, A. Kydonieus, ed., Marcel Dekker, Inc. New York, N.Y., pp. 315-339, (1992) both of which are incorporated herein by reference.

Polymers can be used for ion-controlled release of the active agents disclosed herein. Various degradable and non-degradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., Pharm. Res. 9:425-434, 1992; and Pec et al., J. Parent. Sci. Tech. 44(2):58-65, 1990). Alternatively, hydroxyapatite has been used as a microcarrier for controlled release of proteins (Ijntema et al., Int. J. Pharm. 112:215-224, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

The actives may be administered orally. An active may be administered orally in a liquid dosage form or a solid dosage form. Examples of solid dosage forms are tablets, capsules, granules, powders, beads and microcapsules. An active agent of the disclosure, with or without at least one additional therapeutic agents, that is administered in a solid dosage may be formulated with or without those carriers customarily used in the compounding of solid dosage forms such as tablets and capsules. A solid oral dosage form may be designed to release the active portion of the formulation at the point in the gastrointestinal tract where bioavailability is maximized and pre-systemic degradation is minimized. At least one additional agent may be included to facilitate absorption of an active of the disclosure and/or any additional therapeutic agents. In such solid dosage forms, the active compound is typically mixed with at least one inert, pharmaceutically acceptable excipient or carrier such as lactose, sodium citrate or dicalcium phosphate and/or one or more: a) fillers or extenders for example starches, lactose, sucrose, glucose, mannitol and silicic acid; b) binders for example carboxymethylcellulose, alginates, gelatin, polyvinylpyrrolidone, sucrose and acacia; c) humectants for example glycerol; d) disintegrating agents for example agar-agar, calcium carbonate, potato or tapioca starch, alginic acid, certain silicates and sodium carbonate; e) solution retarding agents for example paraffin; f) absorption accelerators for example quaternary ammonium compounds; g) wetting agents for example cetyl alcohol and glycerol monostearate; h) absorbents for example kaolin and bentonite clay and i) lubricants for example talc, calcium stearate, magnesium stearate, solid polyethylene glycols, sodium lauryl sulfate and mixtures thereof. Solid compositions of a similar type may also be employed as fillers in soft and hard-filled gelatin capsules using such excipients as lactose or high molecular weight polyethylene glycol, for example.

The compounds of the invention or pharmaceutical composition comprising the active compound may be administered to a subject by any convenient route of administration, whether systemically/peripherally or topically (ie., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, infraarterlal, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

The present invention is now illustrated by way of the following non-limiting examples, and supported by the data herein disclosed.

Materials and Equipment

The following materials used in the Examples outlined herein were obtained from Sigma-Aldrich.

| Name | CAS number |
|---|---|
| Cyanoacetaldehyde dimethyl acetal | 57597-62-3 |
| Cyanoacetaldehyde diethyl acetal | 2032-34-0 |
| Bromoacetaldehyde diethyl acetal | 2032-35-1 |
| Chloroacetaldehyde diethyl acetal | 621-62-5 |
| Cytosine | 71-30-7 |
| Uracil | 66-22-8 |
| 5-Fluorocytosine | 2022-85-7 |
| 5-Fluorouracil | 51-21-8 |
| Urea | 57-13-6 |

Proton, fluorine and carbon nuclear magnetic resonance spectra ($^1$H, $^{19}$F and $^{13}$C NMR) were obtained from a Bruker 400 Ultrashield spectrometer ($^1$H NMR at 400 MHz, $^{19}$F NMR at 376 MHz and $^{13}$C NMR at 101 MHz) using residual solvent peaks as the internal standard ($^1$H NMR; CHCl$_3$ at 7.26 ppm, $^{19}$F NMR; CFCl$_3$ at 0.00 ppm and $^{13}$C NMR; CDCl$_3$ at 77.16 ppm). NMR spectroscopic data are reported as follows: chemical shift (ppm), integration, multiplicity (s=singlet, d=doublet, t=triplet, q=quartet, m=multiplet), coupling constant (Hz) and assignment.

Accurate mass analysis was performed on a Xevo QtoF mass spectrometer (Waters Ltd, UK) with an accurate solids analysis probe (ASAP). Melting point data was obtained using a Gallenkamp apparatus at atmospheric pressure and are uncorrected. Infra-red (IR) spectroscopy was performed on a Perkin Elmer 1600 Series FTIR with an ATR probe.

Example 1—Direct Fluorination of Cytosine Using a Batch Process

Cytosine (1.11 g, 10 mmol) was dissolved in formic acid and was kept at 20° C. in a water bath. Fluorine (10% in N$_2$) was introduced to the vigorously stirred solution at 25 mL/min (7.5 mmol/h). After introducing the desired quantity of fluorine, the solvent was removed in vacuo and the residue was recrystallized from water (10 mL). The formed crystalline product was filtered and analysed using $^1$H and $^{19}$F NMR spectroscopy.

Example 2—Various Direct Fluorination Experiments on Cytosine Using a Continuous Flow Reactor (Microreactor)

A 1 M stock solution of cytosine in formic acid was prepared and used for fluorinations. The solution was introduced to the microreactor at 2 mL/h (2 mmol/h) while the flow of fluorine was set according to Table 3. Fractions were collected for 120 minutes, the solvent was evaporated and the product was recrystallized from water (5 mL). The product was filtered, dried in vacuo and analysed using $^1$H and $^{19}$F NMR spectroscopy.

Example 3—Direct Fluorination of Cytosine Using a Continuous Flow Reactor (Microreactor)

1 M cytosine solution was introduced at 2 mL/h while fluorine (10% in N$_2$) was introduced at 15 mL/min (3.75 mmol/h). The reaction was conducted for 12 minutes, the collected fraction was evaporated and recrystallised from water (4 mL). The crystallised product was filtered and dried to afford tan crystals of 5-fluorocytosine (0.27 g, 52% yield, 99% purity).

Example 4—Direct Fluorination of Cytosine Using a Continuous Flow Reactor with a Stainless Steel Tube Reactor (Larger Scale)

1.0 M cytosine solution in formic acid was introduced at 4.0 mL/h (4.0 mmol/h) while fluorine (10% in N$_2$) was introduced at 20 mL/min (5 mmol/h). The reaction was conducted for 90 minutes, the collected fraction was evaporated and the residue was recrystallized from water (7 mL). After filtration, the product was dried under reduced pressure to afford 5-fluorocytosine (0.49 g, 63% yield) as a tan powder. M.p.: 295-300° C. (decomposes), ([M]+129.0337, [M]$^+$ requires: 129.0338); IR (cm$^{-1}$): 3384, 3092, 2724, 1665, 1624, 1551, 1454, 1216; $^1$H NMR (400 MHz, D$_2$O+DCl) 7.83 (1H, d, $^3J_{HF}$ 4.8 Hz); $^{19}$F NMR (400 MHz, D$_2$O+DCl) −169.7 (1F, d, $^3J_{HF}$ 4.8 Hz); $^{13}$C NMR (100 MHz, D$_2$O+DCl): 130.67 (d, $^2J_{CF}$ 29.6 Hz), 135.25 (d, $^1J_{CF}$ 232 Hz), 147.88, 153.65 (d, $^2J_{CF}$ 23.4 Hz); MS (ASAP): 111 (37%, [M+H−F]$^+$), 129 (8%, [M]$^+$), 130 (100%, [M+H]$^+$).

Results and Discussion

The inventors pursued a 3 step strategy involving the synthesis of cytosine from commodity chemicals and subsequent direct fluorination, and assessed this shortened synthetic route for suitability for scale-up and green metrics.

Scheme 2 - Inventors proposed synthesis of flucytosine

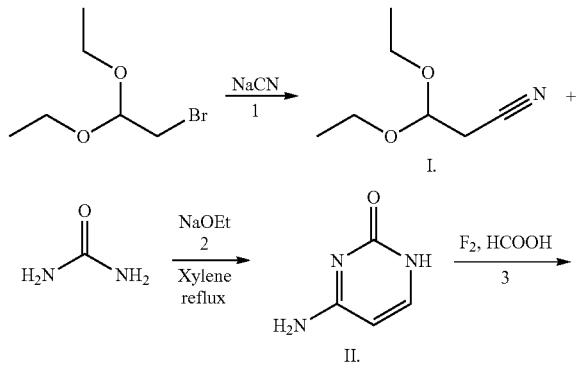

-continued

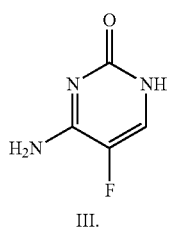

III.

The first step involves bromoacetaldehyde diethyl acetal reacting with sodium cyanide in DMSO, to afford the desired product in 80% yield after distillation, which was reported in the literature (J. Am. Chem. Soc. 1975, 97, 7152-7157 (80% yield, NaCN, DMSO); J. Org. Chem. 1945, 10, 76-85 (low yield); Just. Leib. Ann. Chem. 1978, 1946-1962). This reaction uses very concentrated conditions for the reaction, which is promising for scale-up.

The second step describes how cytosine is obtained by condensation of urea and cyanoacetaldehyde diethyl acetal in good yield using toluene or xylenes as solvent. This step has also been previous reported (U.S. Pat. No. 5,026,852).

Step 3 was key to the inventors' investigations. A number of methods for the fluorination of cytosine are disclosed in the literature, but most are obsolete due to their use of reagents that are no longer available ($CF_3OF$) (J. Chem. Soc. Chem. Comm. 1972, 18). Direct fluorination of cytosine has been mentioned elsewhere in the literature, but the only procedure for direct fluorination where the product was isolated uses anhydrous hydrogen fluoride as solvent at −50° C. which makes this process very hazardous and difficult to handle (Eur. Pat. Appl. 63352, 1982). In another publication [$^{18}F$]$F_2$ was used by Visser et al. to examine the mechanism of direct fluorination of cytosine in acetic acid with radio-labelled $^{18}F$—fluorine. The formation of Flucytosine was observed in low (20-25%) radiochemical yield along with various other fluorinated heterocycles (J. Chem. Soc. Perkin 1., 1988, 1203; J. Org. Chem. 1986, 1466).

Step 1: Synthesis of Cyanoacetaldehyde Diethyl Acetal Using Cyanide Sources

Scheme 3 - Synthesis of cyanoacetaldehyde diethyl acetal using cyanide.

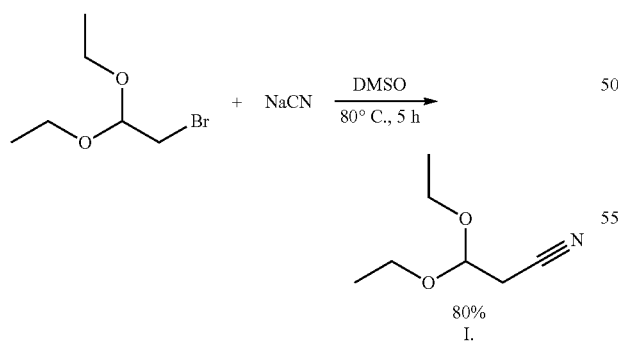

By a literature process, cyanoacetaldehyde diethyl acetal is efficiently prepared from bromoacetaldehyde diethyl acetal and sodium cyanide (J. Am. Chem. Soc. 1975, 97, 7152-7157). The reaction was conducted in dimethyl sulfoxide at 80° C. than worked up by quenching with water and extracting the product with ether. After washing the ether extracts multiple times with brine, the product was isolated in 80% yield after a vacuum distillation. This reaction demonstrates that this strategy is potentially viable.

Step 2: Synthesis of Cytosine

Figure 7:
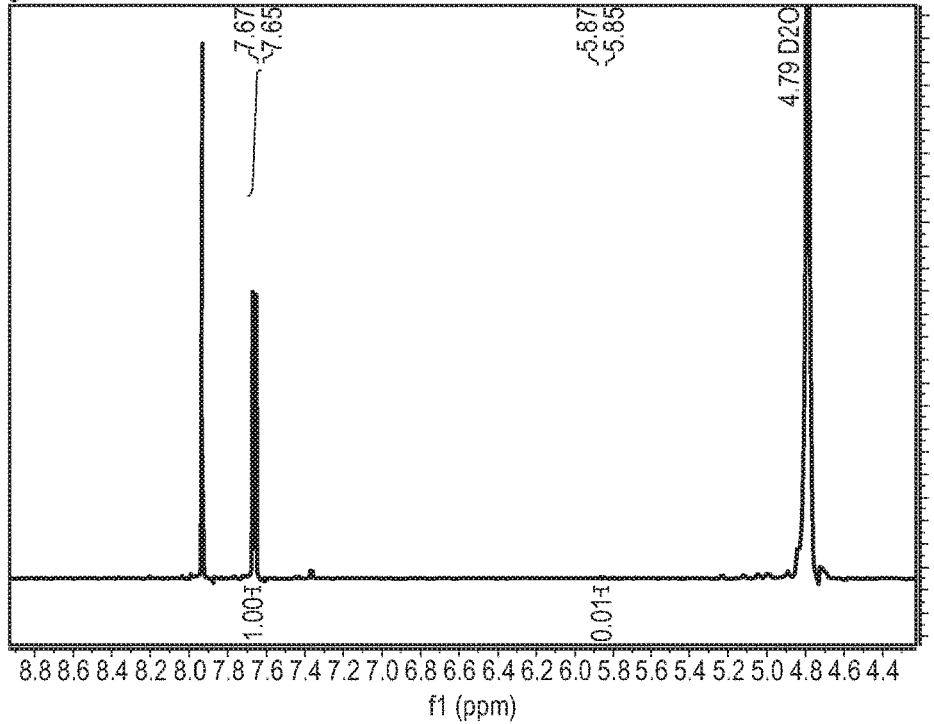
FIG. 7 is an $^{19}$F NMR spectrum of crude product mixture from fluorination of cytosine using stainless steel tube continuous flow apparatus showing presence of difluorinated side product

The literature synthesis (U.S. Pat. No. 5,026,852) of cytosine was repeated at Durham on 0.1 mol (11 g) scale and after recrystallisation, pure cytosine was obtained in 57% yield. In this reaction, cyanoacetaldehyde diethyl acetal was added to the refluxing mixture of urea and sodium ethoxide in m-xylene over an hour using a dropping funnel. After refluxing for three hours, ethanol was distilled from the mixture, the mixture cooled to room temperature and water was added to dissolve the cytosine sodium salt. After separating the phases, the aqueous phase was neutralised with one equivalent of acetic acid and the residue was allowed to crystallise. The crystalline product was filtered, washed with water and dried under reduced pressure. The cytosine obtained this way was sufficiently pure for further use in fluorination reactions. Without recrystallization, the product has a yellow colour, but no significant impurities (>1%) were detected by $^1H$ NMR spectroscopy (FIG. 7).

FIG. 1 shows a $^1H$ NMR of crude non-recrystallised cytosine.

In another batch, where mechanical stirring was used on 20 g scale, the crude product was obtained in 89% yield. In the original publication the solvent (xylenes) was recycled in a next batch without any treatment which resulted in slightly improved yield. An alternative, greener solvent p-cymene, derived from natural product limonene, was examined and cytosine was obtained in 67% unoptimised yield. With optimisation and intensification, this reaction can become a green process. Clearly an industrially based process development department would be able to improve on the yield given sufficient investment.

Scheme 4 - Synthesis of cytosine from cyanoacetaldehyde and urea

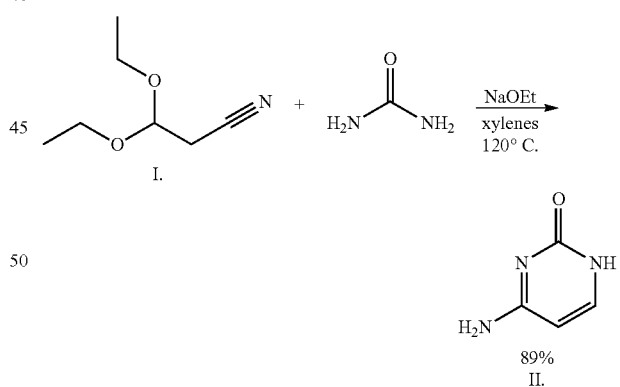

Step 3: Synthesis of Flucytosine

It was found that cytosine was soluble in formic acid, a preferred medium for direct fluorination due to enhanced reaction control, and the most concentrated solution prepared so far was 160 g/L (1.45 M) and promising for future process intensification.

Conventional Batch Process

Batch fluorinations were conducted in our standard 100 mL fluorination reactor. Cytosine was dissolved in formic acid in the batch reactor and was fluorinated with 10% fluorine in nitrogen at 40 mL/min (10 mmol/h). The reaction at room temperature with 10% fluorine in nitrogen yields a crude mixture that contains mainly the desired product (approx. 50% by $^{19}$F NMR spectroscopy, δ–170 ppm, doublet) and one major difluorinated side product (δ–114 (dd, $^2J_{FF}$ 279 Hz, $^3J_{HF}$ 6 Hz) –131 ppm (dd, $^2J_{FF}$ 279 Hz, $^3J_{HF}$ 3 Hz)) along with several other side products (FIG. 2).

Figure 2:
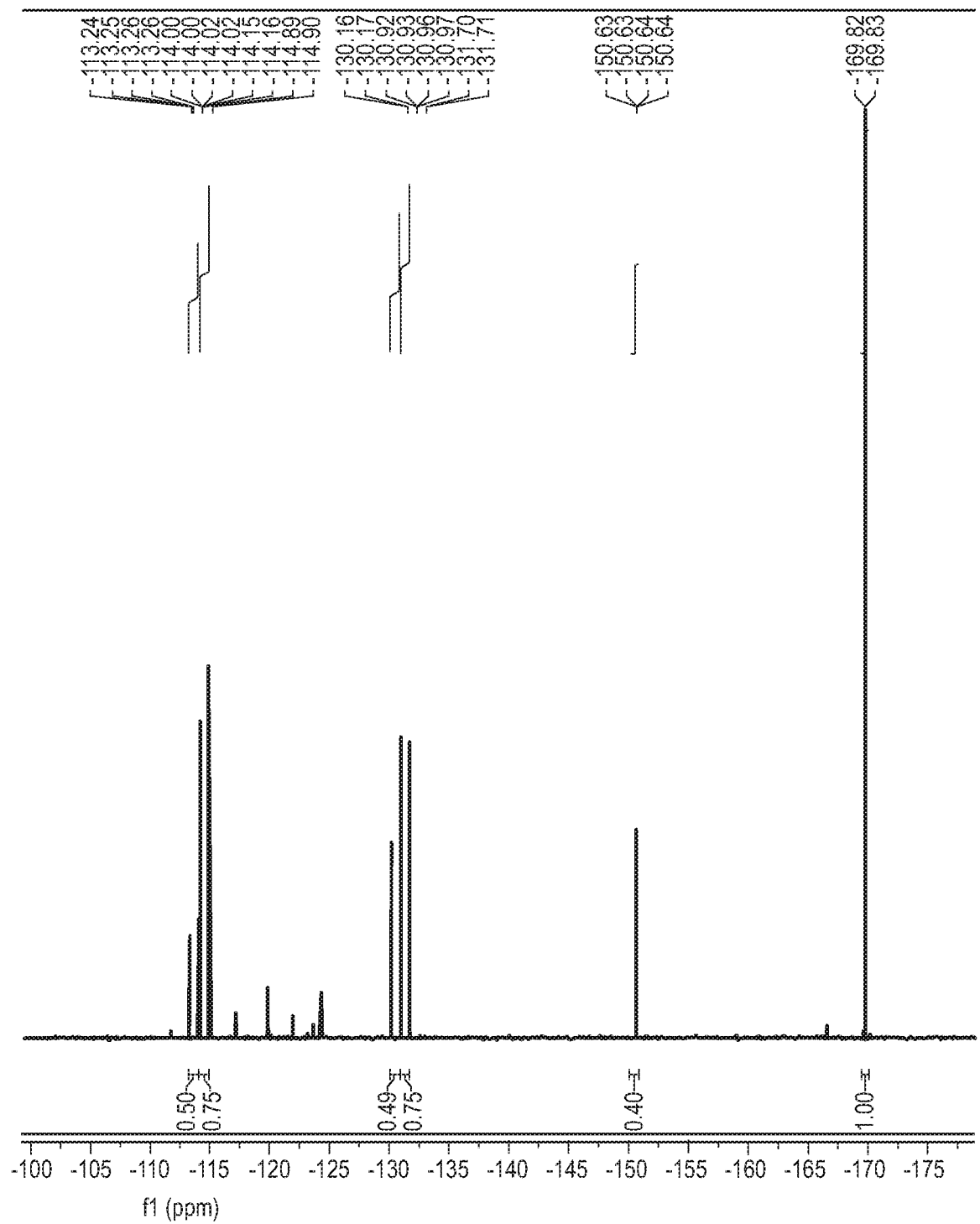
FIG. 2 shows a crude $^{19}$F NMR of product mixture recovered after batch fluorination.

FIG. 2 shows a crude $^{19}$F NMR of product mixture recovered after batch fluorination.

The difluorinated side product IV has been suggested in the literature before, but no $^{19}$F NMR data is available. The two fluorine atoms are not equivalent, hence the large F-F coupling and the difference between the H-F couplings.

Table 2 demonstrates the conversion of cytosine at increasing amounts of fluorine. As the excess of fluorine increases so does the amount of the difluorinated side product.

TABLE 1

Batch fluorination of cytosine.

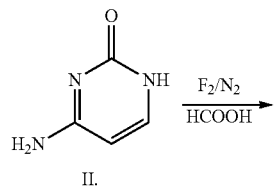

| F$_2$ equivalents | Conversion ($^1$H NMR) | III. to IV. ratio in crude product ($^{19}$F NMR) |
|---|---|---|
| 1.0 | 90% | 2.5:1 |
| 1.5 | 98% | 1:1.1 |
| 1.75 | 99%+ | 1:1.3 |

Figure 3:
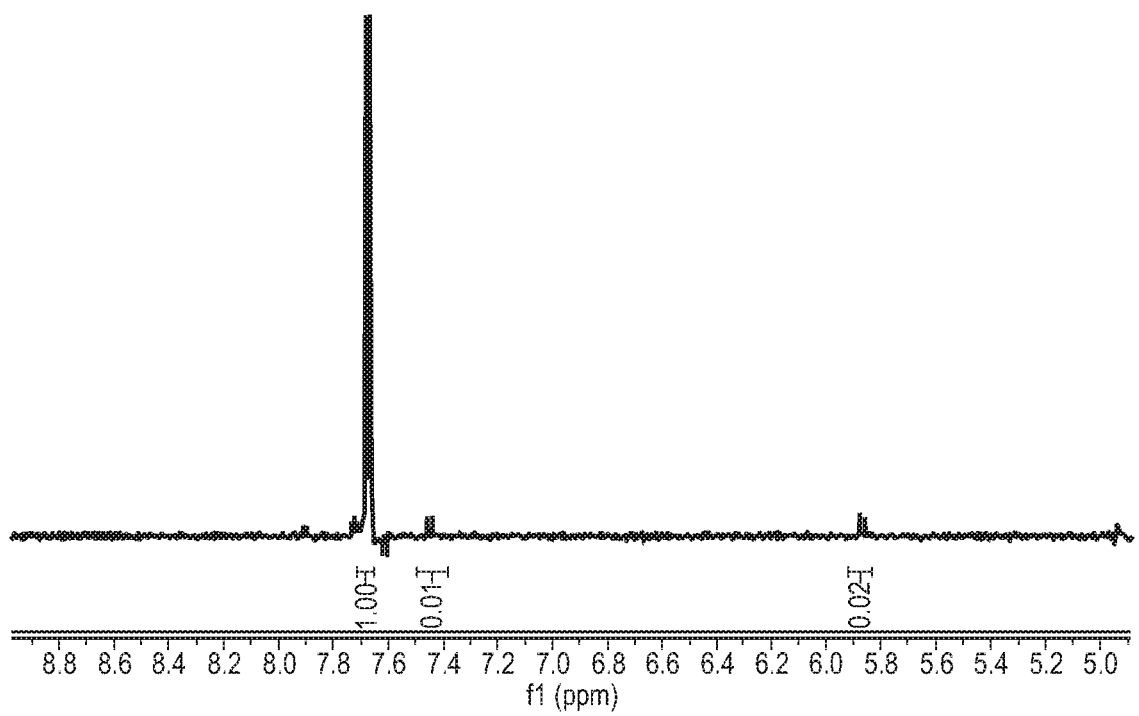
FIG. 3 shows an $^1$H NMR of flucytosine synthesised by batch fluorination.
Figure 4:
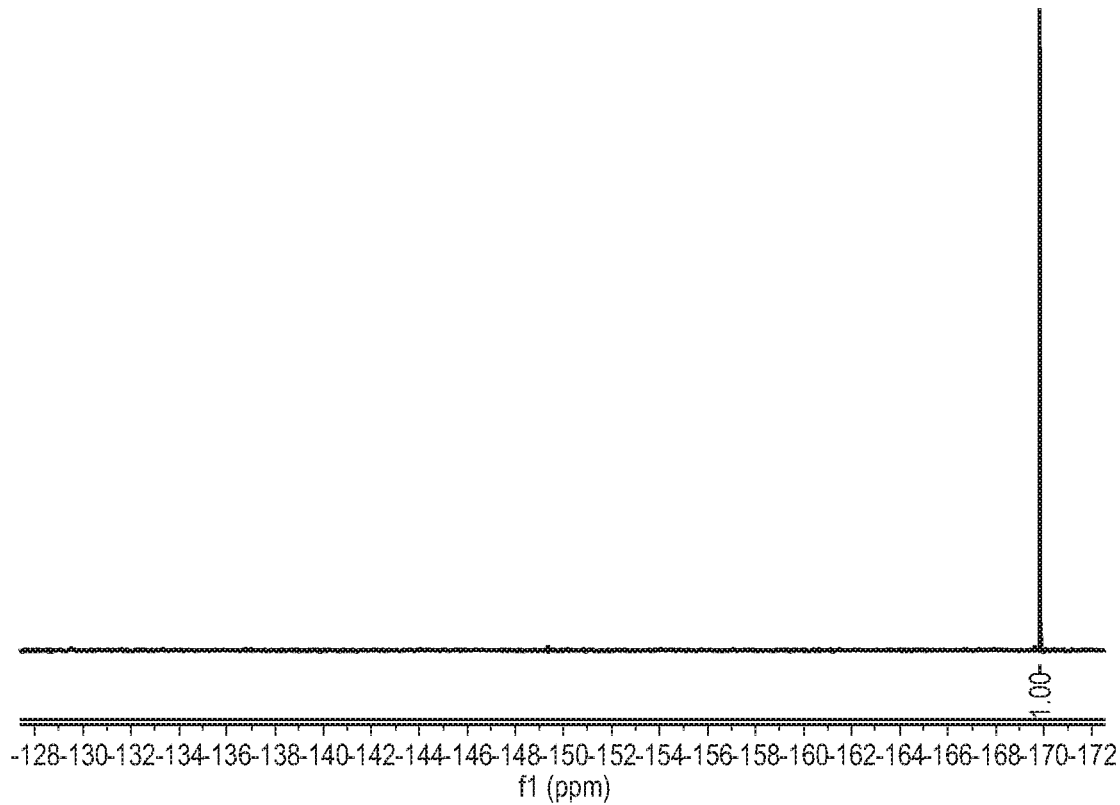
FIG. 4 shows an $^{19}$F NMR of flucytosine synthesised by batch fluorination.

Recrystallization efficiently removes all difluorinated organic impurities, but the separation of unreacted starting material from the desired flucytosine product is very difficult. Therefore, the reaction has to be run to 100% conversion. In this case, after recrystallization from water, the desired monofluorinated product can be isolated as the only fluorinated product (FIGS. 3 and 4). After all starting material was consumed, Flucytosine was isolated in 38% yield after a crystallisation from water. Based on $^{19}$F NMR spectroscopic experiments, the recovery of 5-fluorocytosine from the aqueous recrystallization is excellent, as the liquor only contains trace amounts of the desired product.

FIG. 3 shows an $^1$H NMR of flucytosine synthesised by batch fluorination.

FIG. 4 shows an $^{19}$F NMR of flucytosine synthesised by batch fluorination.

In conclusion, these preliminary findings demonstrate that batch fluorination processes can be used to synthesise Flucytosine in good yield although the formation of significant quantities of difluorinated product leads to considerable waste. The use of continuous flow reactors may lead to different product profiles and fluorination of cytosine in various flow reactor systems were studied as described below.

Continuous Flow Processes—Single Channel Reactor (0.5 mm Channel Width)

Figure 5:
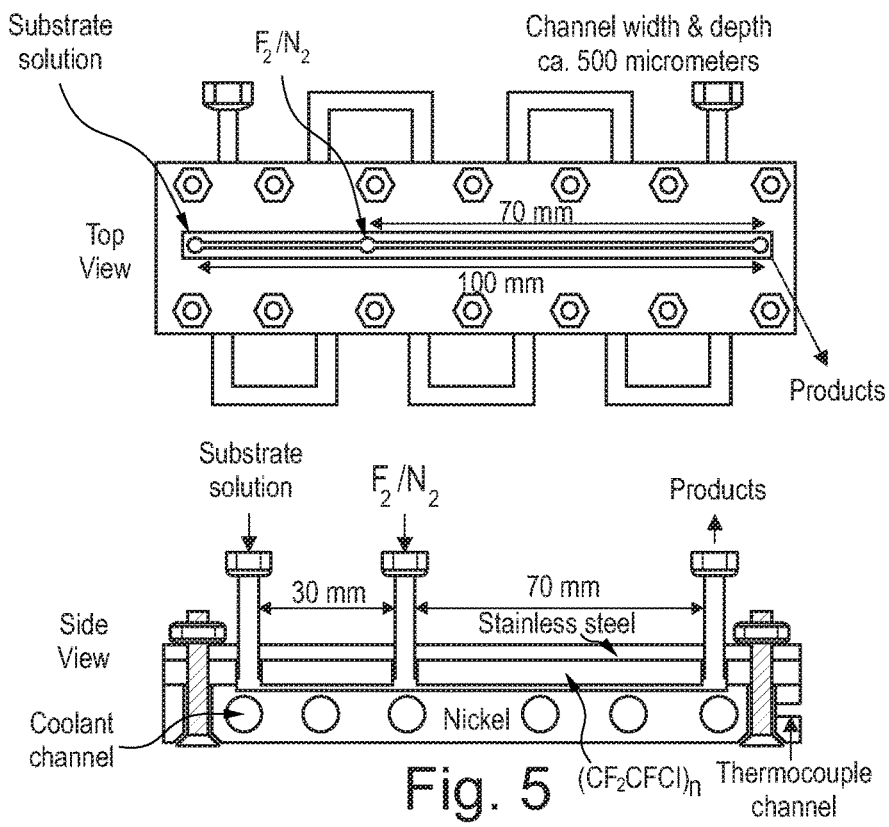
FIG. 5 shows a schematic representation of the single channel microreactor used in continuous flow fluorination of cytosine.

The single channel microreactor was developed in our laboratory for selective fluorination using elemental fluorine (FIG. 5). The reactor is built from a nickel or stainless steel plate having a 0.5 mm deep and 0.5 mm wide channel which is covered with a transparent fluoropolymer (poly(chlorotrifluoroethylene)) and a stainless steel plate. The reactor is also equipped with heat exchanger channels to enable efficient cooling if needed. The solution of the substrate in an appropriate solvent is introduced via a syringe pump, while fluorine gas is introduced via a mass-flow controller. The mixture from the reactor is collected in a round bottomed flask connected to a soda lime scrubber that is used to neutralise excess fluorine.

FIG. 5 shows a schematic representation of the single channel microreactor used in continuous flow fluorination of cytosine.

Using the continuous flow microreactor system, cytosine was fluorinated with 10% fluorine gas in nitrogen. Screening of fluorine to cytosine flows shows that 1.5 equivalents of fluorine gas result in full conversion of cytosine and pure Flucytosine is obtained in much better yield than analogous reactions in batch. The reactions were run for approximately two hours (2 mmol/h cytosine flow), the solvent evaporated and the crude product recrystallized from 4 mL of water and the final product composition was determined by $^1$H and $^{19}$F NMR spectroscopy.

TABLE 2

Continuous flow fluorination of cytosine.

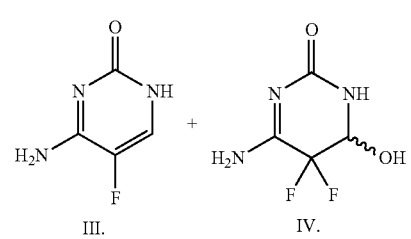 [SMILES: Nc1nc(=O)[nH]cc1F ; NC1=NC(=O)NC(O)C1(F)F]

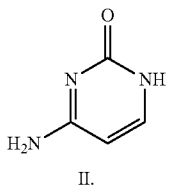

| Cytosine flow | Fluorine flow | Crude product II.:III.:IV. | Crystallised product II.:III. ($^1$H | |
|---|---|---|---|---|
| (1M in HCOOH) | (10% in N$_2$), eq. | ($^1$H and $^{19}$F NMR) | NMR) | Yield (g, %) |
| 2 mL/h (2 mmol/h) | 8 mL/min (2.0 mmol/h), 1.0 | 1:10:1 | 1:9 | 0.32 g, 62% |
| 2 mL/h (2 mmol/h) | 10 mL/min (2.5 mmol/h) 1.5 | 1:17:1.5 | 1:14 | 0.31 g, 61% |
| 2 mL/h (2 mmol/h) | 12 mL/min (3.0 mmol/h) 1.75 | 1:89:9* | >99% pure III. | 0.27 g, 52% |

*Some other unidentified fluorinated side products also observed.

The $^1$H NMR spectrum of one the crude products for all reactions showed that there is a significantly smaller amount of difluorinated side product (IV.) in the mixture, which clearly demonstrates the advantage of flow systems over batch reactions due to decreased contact time between $F_2$ and reaction mixture.

Continuous Flow Processes—Wide Bore (1.4 mm ID) Stainless Steel Tube Fluorinations Despite having several multi-channel reactors that were developed for fluorinations, scaling up in microreactors can be challenging. Rather than multiplying the number of channels, increasing the diameter and the volume of the reactor could offer another, simpler option for scaling up. When the reaction was performed in a standard, coiled 1 m long stainless steel tube (1.4 mm ID) similar isolated yield (63%) and complete conversion of the starting material was observed at 4 mmol/h rate. The better conversion and lower fluorine excess can possibly be explained by the significantly longer residence time of the two reactors (approx. 5 minutes vs. 10-15 seconds). It should be noted that these residence times relate to the liquid phase residence time (i.e. cytosine in acid). The gas and liquid phases are substantially immiscible.

TABLE 3

Fluorination of cytosine in the stainless steel tube reactor.

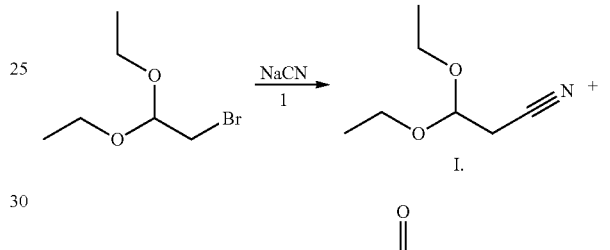

| Cytosine flow | Fluorine flow | Crude product II.:III.:IV. | Crystallised product | |
|---|---|---|---|---|
| (1M in HCOOH) | (10% in $N_2$), eq. | ($^1$H and $^{19}$F NMR) | II.:III. ($^1$H NMR) | Yield (g, %) |
| 4 mL/h (4 mmol/h) | 16 mL/min (4.0 mmol/h), 1.0 | 1:19.5:1.5 | 1:17.5 | 0.51 g, 66% |
| 4 mL/h (4 mmol/h) | 18 mL/min (4.5 mmol/h) 1.12 | 1:71:5 | 1:79 | 0.50 g, 64% |
| 4 mL/h (4 mmol/h) | 20 mL/min (5.0 mmol/h) 1.25 | 1:99:3 | >99% pure III. | 0.46 g, 59% |
| 4 mL/h (4 mmol/h)* | 20 mL/min (5.0 mmol/h) 1.25 | 1:99:5 | >99% pure III. | 0.49 g, 63% |

*HPLC pump used instead of syringe pump.

Figure 6:
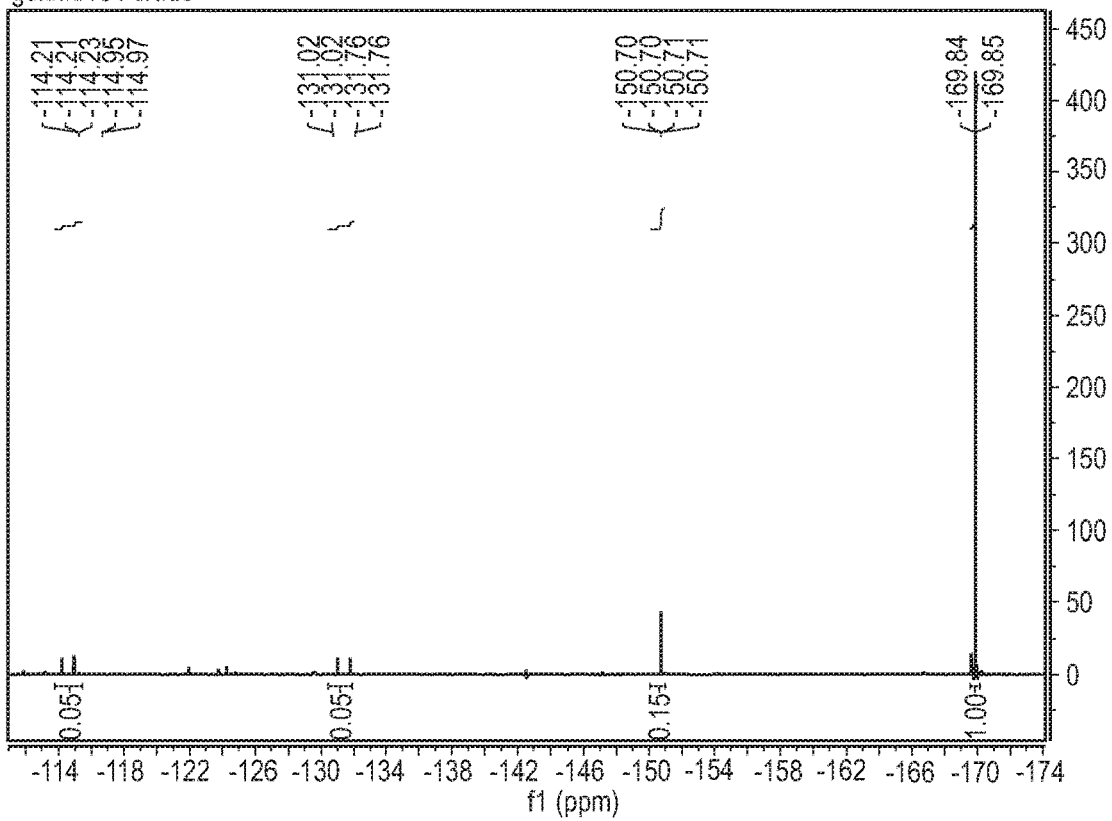
FIG. 6 is an $^1$H NMR spectrum of crude product mixture from fluorination of cytosine using stainless steel tube continuous flow apparatus showing presence of difluorinated side product.

FIG. 6 is an $^1$H NMR spectrum of crude product mixture from fluorination of cytosine using stainless steel tube continuous flow apparatus showing presence of difluorinated side product.

FIG. 7 is an $^{19}$F NMR spectrum of crude product mixture from fluorination of cytosine using stainless steel tube continuous flow apparatus showing presence of difluorinated side product.

Figure 8:
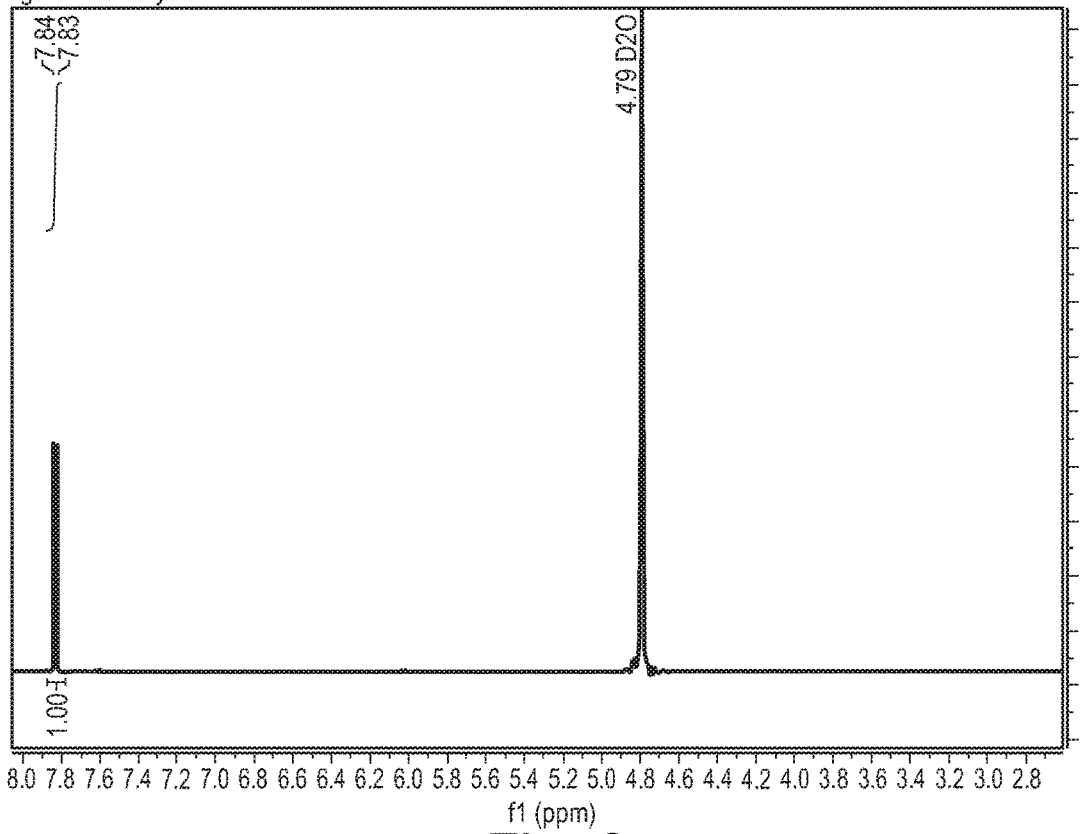
FIG. 8 is an $^1$H NMR spectrum of pure Fluorcytosine synthesised using stainless steel tube continuous flow apparatus.

FIG. 8 is an $^1$H NMR spectrum of pure Fluorcytosine synthesised using stainless steel tube continuous flow apparatus.

Figure 9:
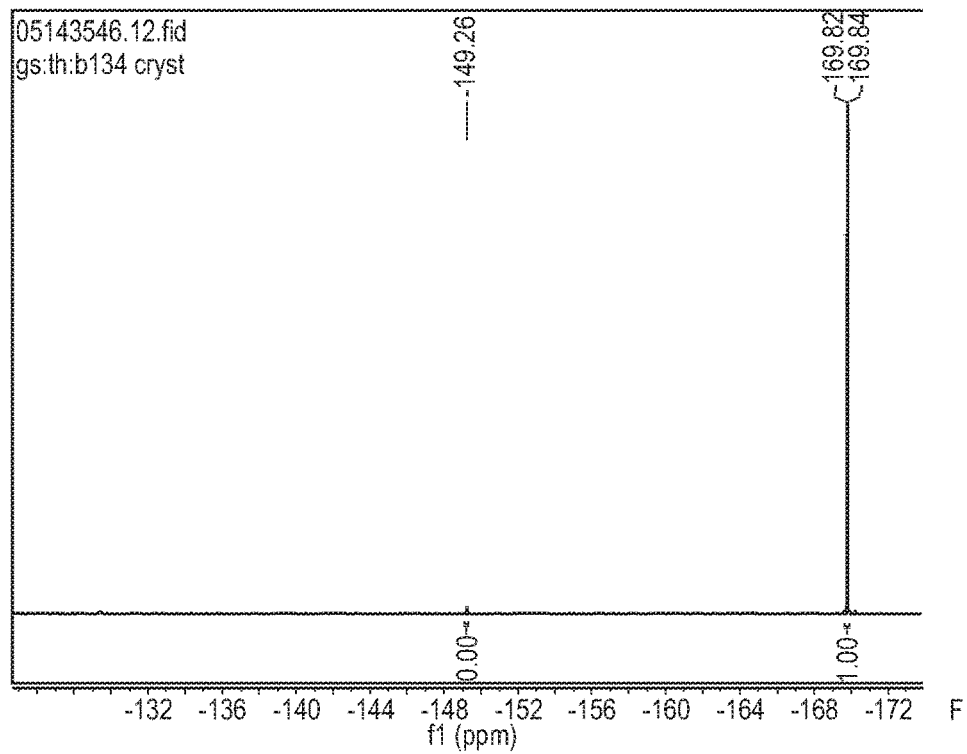
FIG. 9 is an $^{19}$F NMR spectrum of pure Fluorcytosine synthesised using stainless steel tube continuous flow apparatus.

FIG. 9 is an $^{19}$F NMR spectrum of pure Fluorcytosine synthesised using stainless steel tube continuous flow apparatus.

Figure 10:
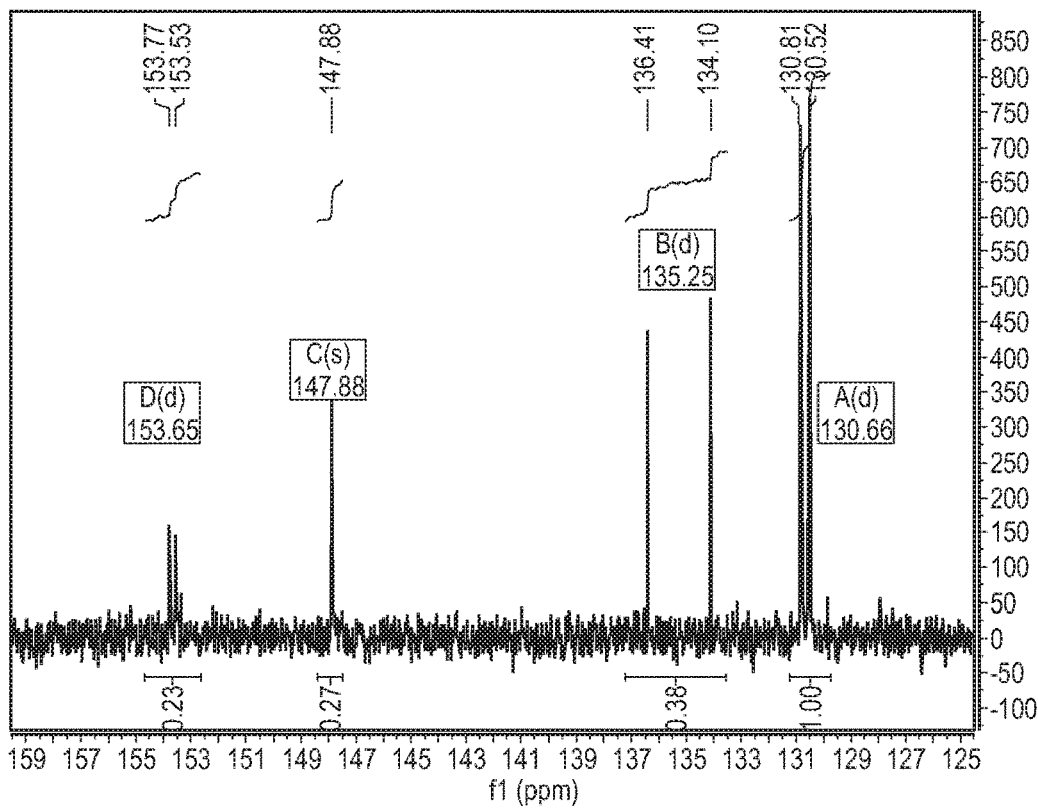
FIG. 10 is a $^{13}$C NMR spectrum of pure Fluorcytosine synthesised using stainless steel tube continuous flow apparatus.

FIG. 10 is a $^{13}$C NMR spectrum of pure Fluorcytosine synthesised using stainless steel tube continuous flow apparatus.

Figure 11:
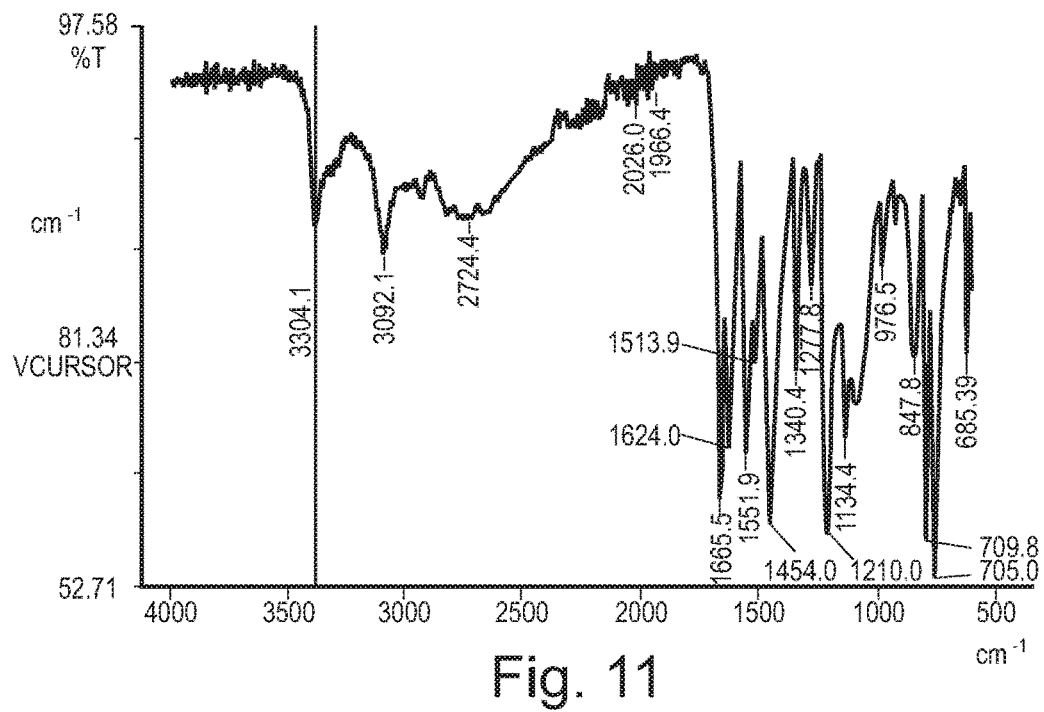
FIG. 11 is an infra-red spectrum of pure Fluorcytosine synthesised using stainless steel tube continuous flow apparatus.

FIG. 11 is an infra-red spectrum of pure Fluorcytosine synthesised using stainless steel tube continuous flow apparatus.

Figure 12:
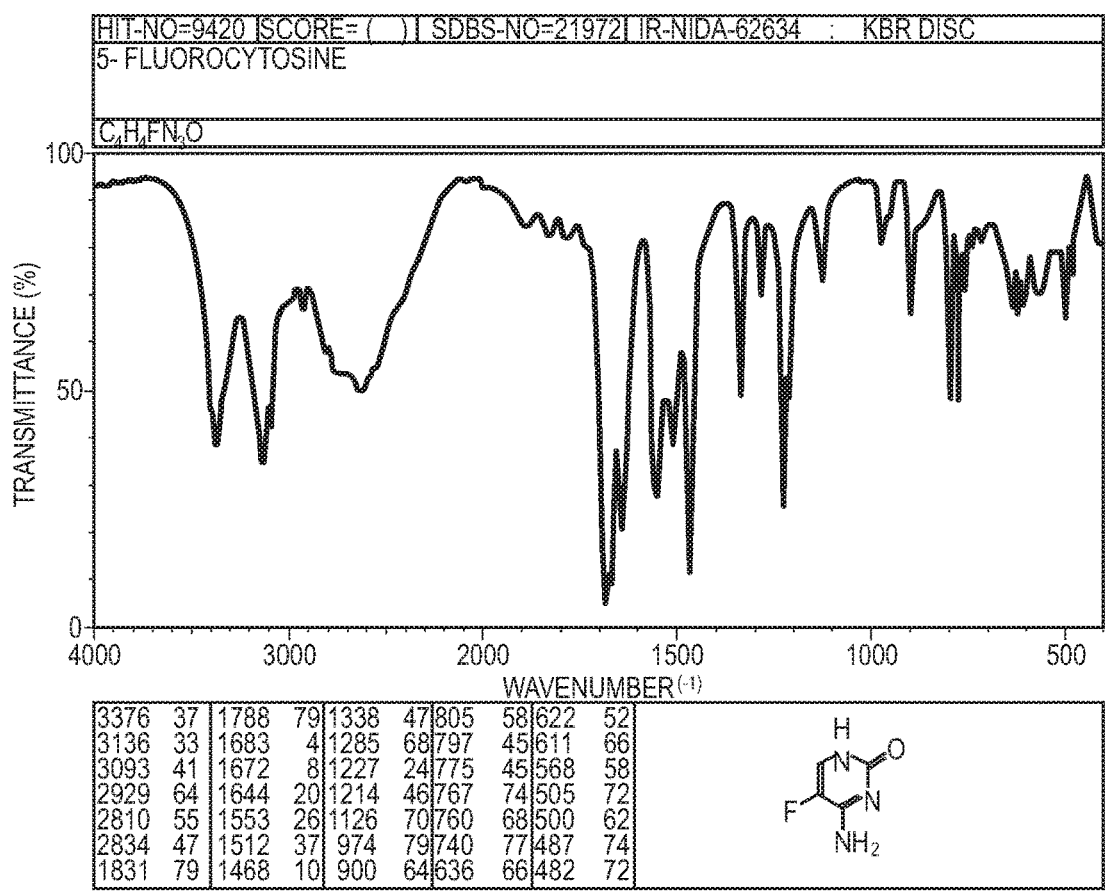
FIG. 12 is an SDBS IR library spectrum of fluorcytosine for comparison.

FIG. 12 is an SDBS IR library spectrum of fluorcytosine for comparison.

Green Metrics of IMI Method for Flucytosine

Using our initial data, obtained from relatively small scale processes, we were able to compute PMI metrics for comparison with established Flucytosine synthesis from 5-fluorouracil. Data for both the synthesis and fluorination of cytosine is presented in Table 4.

TABLE 4

PMI metrics of the Durham/IMI process.

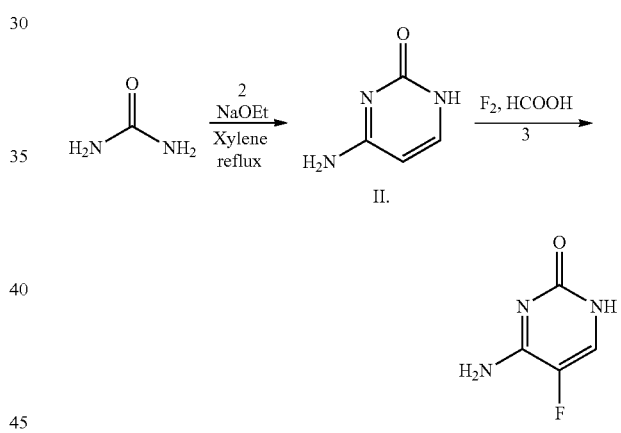

| Step Name/Number | Cytosine | Fluorination (tube reactor) |
|---|---|---|
| Mass Substrate (g) | 44.22 | 0.66 |
| Mass Reagents (g) | 30.73 | 0.28 |
| Mass Solvents (g) | 60.00 | 5.40 |
| Mass Aqueous (g) | 70.00 | 7.00 |
| Step PMI | 10.35 | 27.22 |
| Step PMI Substrate, Reagents, Solvents | 6.81 | 12.94 |
| Step PMI Substrates and Reagents | 3.78 | 1.92 |
| Step PMI Solvents | 3.03 | 11.02 |
| Step PMI Water | 3.53 | 14.29 |
| Cumulative PMI | 10.35 | 39.81 |
| Cumulative PMI Substrate, Reagents, Solvents | 6.81 | 20.77 |
| Cumulative PMI Substrates and Reagents | 3.78 | 5.67 |
| Cumulative PMI Solvents | 3.03 | 15.10 |
| Cumulative PMI Water | 3.53 | 19.05 |

The process metrics look promising, considering that only initial small scale reactions have been carried out and we can reasonably expect better yields and product recovery on scale up. The PMI for these two steps is ca. 40 as compared to 87 for the three step synthesis from 5 FU. The biggest waste source is water (48% of PMI), as the first step involved a precipitation from aqueous solution and after fluorination the product is purified by recrystallisation from water (approx. 10 mL/g).

The use of organic solvents is not excessive and both solvents can be recycled. Realistically, the optimisation of water and solvent consumption should further decrease the cumulative PMI and as recovered/reused solvents can be subtracted from the overall values.

CONCLUSIONS

The methods of the invention provide significant advantages over the prior art, including:
A maximum of 3 steps from commodity chemicals
all chemicals are inexpensive
potential applications to flow processes (fluorination stage), minimising losses of valuable fluorinated material in a multi-step process
fluorination occurs in the final step (late-stage)
solvents, reaction conditions and waste are more environmentally benign
scale-up commercially attractive given high volume and value of Flucytosine for various drug packages

The invention claimed is:

1. A method of manufacturing a compound of Formula I, or a salt or solvate thereof:

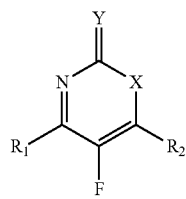

(Formula I)

the method comprising reacting a compound of Formula II:

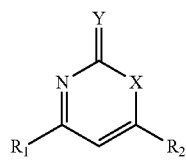

(Formula II)

with an electrophilic fluorinating agent wherein the electrophilic fluorinating agent is fluorine gas, optionally provided as a gaseous composition (i.e. corresponding to a second input load) comprising fluorine and optionally one or more carrier gases;
wherein:
X is $NR_x$, O, or S; wherein $R_x$ is hydrogen or is independently selected from any $R_N$ group;
Y is O, S, or $NR_y$; wherein $R_y$ is hydrogen or is independently selected from any $R_N$ group;
$R_1$ is hydrogen or is independently selected from any $R_s$ group, though most suitably $R_1$ is an electron donating group (EDG), most suitably an EDG selected from $NR_{1a}R_{1b}$ or $OR_{1a}$, wherein $R_{1a}$ and $R_{1b}$ are each independently selected from hydrogen or any $R_N$ group;
$R_2$ hydrogen or is independently selected from any $R_s$ group;
each $R_N$ group is independently selected from (1-8C) alkyl, (2-8C)alkenyl, (2-8C)alkynyl, aryl, aryl-(1-6C) alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, formyl, carboxy, (2-6C)alkanoyl, (1-6C)alkoxycarbonyl, carbamoyl, N-(1-6C) alkylcarbamoyl, N,N-di-[(1-6C)alkyl]carbamoyl, (1-6C)alkylsulphinyl, (1-6C)alkylsulphonyl, N-(1-6C) alkylsulphamoyl, N,N-di-[(1-6C)alkyl]sulphamoyl; wherein each $R_N$ group is optionally independently substituted with one or more $R_s$ groups;
each $R_s$ group is independently selected from halogeno, trifluoromethyl, cyano, isocyano, nitro, hydroxy, mercapto, amino, formyl, carboxy, carbamoyl, ureido, (1-8C)alkyl, (2-8C)alkenyl, (2-8C)alkynyl, (1-6C) alkoxy, (2-6C)alkenyloxy, (2-6C)alkynyloxy, (1-6C) alkylthio, (1-6C)alkylsulphinyl, (1-6C)alkylsulphonyl, (1-6C)alkylamino, di-[(1-6C)alkyl]amino, (1-6C) alkoxycarbonyl, (1-6C)alkoxycarbonyloxy, N-(1-6C) alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C) alkenoylamino, N-(1-6C)alkyl-(3-6C)alkenoylamino, (3-6C)alkynoylamino, N-(1-6C)alkyl-(3-6C)alkynoylamino, (1-6C)alkoxycarbonylamino, N-(1-6C)alkyl-(1-6C)alkoxycarbonylamino, N'-(1-6C)alkylureido, N',N'-di-[(1-6C)alkyl]ureido, N-(1-6C)alkylureido, N',N'-di-[(1-6C)alkyl]ureido, N,N',N'-tri-[(1-6C)alkyl] ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$L_1-Q_1$ wherein $L_1$ is a direct bond or is selected from $(CR_{L1} R_{L2})_n$, O, S, SO, $SO_2$, $N(R_{L1})$, CO, $CR_{L1}(O R_{L2})$, $CON(R_{L1})$, $N(R_{L1})CO$, $N(R_{L1})C(O)O$, $N(R_{L1})CON (R_{L2})$, $SO_2N(R_{L1})$, $N(R_{L1})SO_2$, $OC(R_{L1})_2$, $SC(R_{L1})_2$ and $N(R_{L1})C(R_{L2})_2$, wherein n is an integer between 1 and 3, and wherein $R_{L1}$ and $R_{L2}$ are each independently hydrogen or (1-8C)alkyl; and $Q_1$ is (1-8C)alkyl, (2-8C) alkenyl, (2-8C)alkynyl, aryl, aryl-(1-6C)alkyl, (3-8C) cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl;
and wherein any $R_s$ group is independently optionally further substituted by one or more $R_s$ groups;
optionally thereafter transforming a synthetic equivalent of the compound of Formula I (or a salt or solvate thereof) into a compound of Formula I (or a salt or solvate thereof) via one or more chemical transformations;
optionally, and if necessary:
(a) removing any protecting groups present;
(b) converting the compound Formula I into another compound of Formula I; and/or
(c) forming a pharmaceutically acceptable salt thereof;
wherein the reaction between the compound of Formula II and the electrophilic fluorinating agent is performed in a continuous flow reactor.

2. The method as claimed in claim 1, wherein the continuous flow reactor is operated to continuously mix a first input load comprising the compound of Formula II (the first input material) with a second input load comprising the electrophilic fluorinating agent (the second input material) to form a reaction mixture.

3. The method as claimed in claim 1, wherein X is $NR_x$; wherein $R_x$ is hydrogen or is a 5-membered heterocyclyl group optionally substituted with one or more hydroxyl, (1-3C)alkyl, or (1-3C)alkyl substituted with hydroxyl, wherein where $R_x$ is other than hydrogen, $R_x$ forms a hemiaminal ether (or glycosidic) linkage with the nitrogen atom to which it is attached; and/or $R_1$ is independently selected from $NR_{1a}R_{1b}$ or (1-6C) alkoxycarbonylamino, wherein $R_{1a}$ and $R_{1b}$ are each independently selected from hydrogen or (1-6C)alkyl; and/or $R_2$ is hydrogen; and/or each $R_s$ group is independently selected from halogeno, trifluoromethyl, cyano, isocyano, nitro, hydroxy, amino, formyl, carboxy, carbamoyl, ureido, (1-8C) alkyl, (1-6C)alkoxy, (1-6C)alkoxycarbonylamino; wherein any $R_s$ group is independently optionally further substituted by one or more $R_s$ groups as defined in this or any preceding claim.

4. The method as claimed in claim 3, wherein where $R_s$ is substituted with one or more further $R_s$ groups, suitably said further $R_s$ groups are selected from hydroxy, (1-8C)alkyl, hydroxy-(1-8C)alkyl, (1-3C)alkoxy-(1-8C)alkyl, or (1-6C) alkoxy.

5. The method as claimed in claim 1, wherein the compounds of Formula II and Formula I, and a potential impurity compound of Formula I-imp are respectively defined by the structural Formulae IIb, Ib, and Ib-imp shown below:

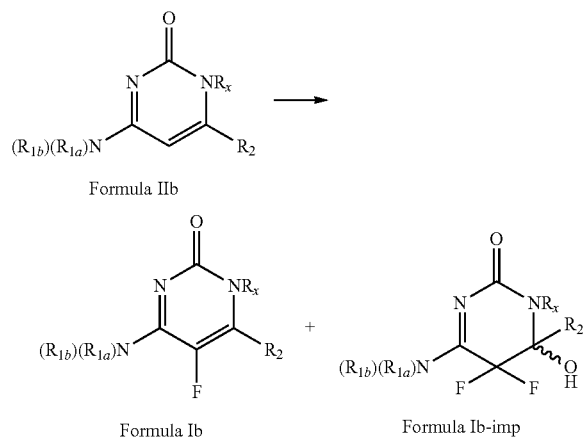

Formula IIb

Formula Ib

Formula Ib-imp or a salt, solvate, or synthetic equivalent of Formula Ib or Formula Ib-imp;

wherein $R_{1a}$, $R_{1b}$, $R_2$, $R_x$, and any groups associated therewith have any one of the meanings defined in claim 1.

6. The method as claimed in claim 1, wherein the compounds of Formula II and Formula I, and a potential impurity compound of Formula I-imp are respectively defined by the structural Formulae IIe, Ie, and/or Ie-imp shown below:

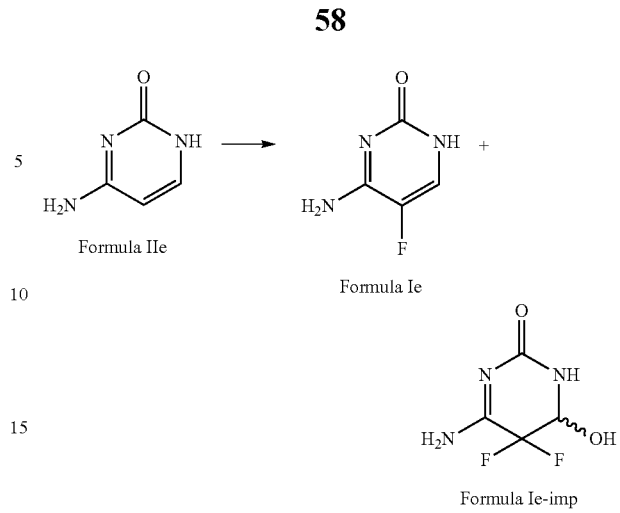

Formula IIe

Formula Ie

Formula Ie-imp or a salt or solvate of Formula Ie or Formula Ie-imp.

7. The method as claimed in claim 1, wherein the compound of Formula I is selected from flucytosine, emtricitabine, or capecitabine, or a pharmaceutically acceptable salt and/or solvate thereof.

8. The method as claimed in claim 1, wherein the electrophilic fluorinating gaseous composition comprises between 1 and 30% fluorine.

9. The method as claimed in claim 8, wherein the electrophilic fluorinating gaseous composition consists essentially of 5 to 15% fluorine and 85 to 95% nitrogen.

10. The method as claimed in claim 2, wherein the first input load comprises the compound of Formula II and a diluent system, wherein the diluent system suitably comprises an acid having a $pK_a$ greater than or equal to 3.17, suitably wherein the diluents system comprises or consists essentially of formic acid.

11. The method as claimed in claim 10, wherein the first input load comprises the compound of Formula II at a concentration between 0.5 M to 1.5 M.

12. The method as claimed in claim 1, wherein the molar ratio of the electrophilic fluorinating agent to compound II is between 1.2:1 and 1.6:1.

13. The method as claimed in claim 2, wherein the volumetric residence time of the reaction mixture is between 1 second and 10 seconds, where the residence time is calculated as:

$$T_r = V_r / F_o$$

where $T_r$ is the residence time given in units of time, $V_r$ is the internal volume of a region within the continuous flow reactor during which a reaction between the first and second input materials occurs (i.e. internal volume of an internal reactor) given in units of volume, and $F_o$ is overall volumetric flow rate given in units of volume per unit time.

14. The method as claimed in claim 1, wherein an output load comprises:
  100 parts by moles compound of Formula I
  1-20 parts by moles compound of Formula I-imp
  0.1-5 parts by moles compound of Formula II or
  100 parts by moles compound of Formula I
  2-10 parts by moles compound of Formula I-imp.

15. The method as claimed in claim 1, wherein an output load is collected as the "collected output load", which is then isolated and/or purified, either partially or fully, to yield a purified product comprising:
  100 parts by moles compound of Formula I
  0-2 parts by moles compound of Formula I-imp 0-2 parts by moles compound of Formula II.

16. The method as claimed in claim 1, wherein the molar yield of the purified product (by reference to the quantity of input material compound of Formula II) is greater than or equal to 60%.

17. The method of claim 1, further comprising:
   optionally performing one or more further step or steps to produce the pharmaceutical drug substance (or a pharmaceutically acceptable salt, solvate, or synthetic equivalent thereof) from the compound of Formula I, or a salt or solvate thereof;
   optionally transforming a synthetic equivalent of the pharmaceutical drug substance (or a salt or solvate thereof) into another pharmaceutical drug substance (or a salt or solvate thereof) via one or more suitable chemical transformations (e.g. deprotections); and
   optionally, and if necessary:
   (a) removing any protecting groups present;
   (b) converting the pharmaceutical drug substance into a different pharmaceutical drug substance; and/or
   (c) forming a pharmaceutically acceptable salt thereof.

18. The method as claimed in claim 17, wherein the pharmaceutical drug substance is selected from flucytosine, emtricitabine, capecitabine, or a pharmaceutically acceptable salt or solvate thereof.

19. The method as claimed in claim 18, wherein the method comprises:
   manufacturing flucytosine, or a salt or solvate thereof, by the method as claimed in claim 1;
   N-coupling flucytosine, via an internal ring nitrogen (NH) thereof, with 2-(hydroxymethyl)-1,3-oxathiolan-5-ol to form a corresponding N-cyclic hemiaminal ether, by reacting flucytosine or a derivative thereof with 2-(hydroxymethyl)-1,3-oxathiolan-5-ol or a derivative thereof;
   and optionally, and if necessary:
   (a) removing any protecting groups present;
   (b) forming a pharmaceutically acceptable salt thereof.

20. The method as claimed in claim 18, wherein the method comprises:
   manufacturing flucytosine, or a salt or solvate thereof, by the method as claimed in claim 1;
   N-coupling flucytosine, via an internal ring nitrogen (NH) thereof, with 5-methyltetrahydrofuran-2,3,4-triol to form a corresponding N-cyclic hemiaminal ether, by reacting flucytosine or a derivative thereof with 5-methyltetrahydrofuran-2,3,4-triol or a derivative thereof;
   N-coupling the N-cyclic hemiaminal ether, via an external nitrogen ($NH_2$) thereof, to a n-pentoxycarbonyl group to form a corresponding carbamate, by reacting the N-cyclic hemiaminal ether with n-pentoxycarbonic acid or a synthetic derivative or activated derivative thereof;
   and optionally, and if necessary:
   (a) removing any protecting groups present;
   (b) forming a pharmaceutically acceptable salt thereof.

* * * * *